(12) United States Patent
Lozano-Buhl et al.

(10) Patent No.: US 10,945,673 B2
(45) Date of Patent: **\*Mar. 16, 2021**

(54) MEDICAL ILLUMINATOR MOBILE DEVICE ATTACHMENT APPARATUS AND METHOD

(71) Applicant: 3GEN, INC., San Juan Capistrano, CA (US)

(72) Inventors: Gregory Paul Lozano-Buhl, Grand Rapids, MI (US); Gregory Edward Mote, Big Bear Lake, CA (US)

(73) Assignee: 3GEN, INC., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,059

(22) Filed: Nov. 7, 2019

(65) Prior Publication Data

US 2020/0237310 A1    Jul. 30, 2020

Related U.S. Application Data

(63) Continuation-in-part of application No. 16/261,239, filed on Jan. 29, 2019, now Pat. No. 10,678,120.

(51) Int. Cl.
*A61B 5/00* (2006.01)
*A61B 90/00* (2016.01)
*A61B 5/05* (2021.01)

(52) U.S. Cl.
CPC .......... *A61B 5/6898* (2013.01); *A61B 5/0077* (2013.01); *A61B 5/0082* (2013.01);
(Continued)

(58) Field of Classification Search
CPC ........... F16B 2001/0035; A61B 5/6898; G03B 17/14
See application file for complete search history.

(56) References Cited

U.S. PATENT DOCUMENTS

| | | | |
|---|---|---|---|
| 2,953,970 | A | 9/1960 | Maynard |
| 3,086,268 | A | 4/1963 | Chaffin |

(Continued)

FOREIGN PATENT DOCUMENTS

| | | |
|---|---|---|
| WO | 2014105649 | 7/2014 |
| WO | 2015035229 | 3/2015 |
| WO | 2020000055 | 1/2020 |

OTHER PUBLICATIONS

Rishpon et al., "Assessment of the Safety Risk of Dermatoscope Magnets in Patients With Cardiovascular Implanted Electronic Devices," JAMA Dermatology, Aug. 15, 2018, American Medical Association, Online publication, 4 pages.

(Continued)

*Primary Examiner* — Noam Reisner
(74) *Attorney, Agent, or Firm* — Stetina Brunda Garred and Brucker

(57) ABSTRACT

The disclosure demonstrates an attachment apparatus for optically coupling a mobile device camera to a lens of a medical examination device. The device incudes an attachment body wherein the proximal side of the attachment body is attached to a mobile device via a magnetic array that may be positioned in at least two different positions. The distal side of the attachment device includes an array of magnets to connect with the lens of a medical device. In one or more of the magnetic arrays at least one pair of axially magnetized magnets are positioned in antiparallel arrangement relative to each other to reduce the expanse of a magnetic field while at the same time increasing the magnetic field strength close to the magnetic poles.

21 Claims, 26 Drawing Sheets

(52) U.S. Cl.
CPC .............. *A61B 5/05* (2013.01); *A61B 90/361* (2016.02); *A61B 5/441* (2013.01)

(56) References Cited

U.S. PATENT DOCUMENTS

| | | | |
|---|---|---|---|
| 6,889,006 | B2 | 5/2005 | Kobayashi |
| 7,600,932 | B2 | 10/2009 | Senba et al. |
| 7,609,465 | B2 | 10/2009 | Wu |
| 8,009,001 | B1 | 8/2011 | Cleveland |
| 8,073,324 | B2 | 12/2011 | Tsai |
| 8,138,869 | B1 | 3/2012 | Lauder et al. |
| 8,639,106 | B1 | 1/2014 | Gleason et al. |
| 8,687,299 | B1 | 4/2014 | Sanford et al. |
| 9,445,713 | B2 | 9/2016 | Douglas et al. |
| 9,484,137 | B2 | 11/2016 | Kocijan |
| 9,706,918 | B2 | 7/2017 | Myung et al. |
| 10,678,120 | B1 * | 6/2020 | Lozano-Buhl ......... G03B 17/14 |
| 2005/0016760 | A1 | 1/2005 | Vasichek |
| 2007/0122145 | A1 | 5/2007 | Chang |
| 2010/0225429 | A1 | 9/2010 | Tsai |
| 2012/0268648 | A1 | 10/2012 | Yang |
| 2013/0163980 | A1 | 6/2013 | Lazaridis et al. |
| 2015/0042877 | A1 * | 2/2015 | O'Neill ................ G03B 17/566 |
| | | | 348/376 |
| 2015/0055279 | A1 | 2/2015 | McBroom et al. |
| 2016/0209365 | A1 | 7/2016 | Tsuda et al. |
| 2016/0282593 | A1 | 9/2016 | Yan |
| 2016/0296112 | A1 | 10/2016 | Fletcher et al. |
| 2017/0090207 | A1 | 3/2017 | Parker |
| 2017/0126943 | A1 | 5/2017 | Fletcher et al. |
| 2017/0280996 | A1 | 10/2017 | Myung et al. |
| 2017/0303857 | A1 | 10/2017 | Perkins et al. |
| 2017/0336619 | A1 | 11/2017 | Cheng |
| 2018/0140196 | A1 * | 5/2018 | Khosravi Simchi ... A61B 90/36 |
| 2020/0367803 | A1 | 11/2020 | Witkowski et al. |

OTHER PUBLICATIONS

"Quick Start Guide," Dermlite Universal Smartphone Adapter, 3Gen, Inc., 2017 (2 pages).
Dermlite Website, "DermLite MagnetiConnect," https://dermlite.com/collections/connection-kits/products/magneticonnect, publication date unknown, site visited Nov. 18, 2019.
Dermlite Website, "DL Connection Kit for iPhone X Series," https://dermlite.com/collections/connection-kits/products/dermlite-connection-kit-for-iphone-x-series?variant=30592803338, site visited Nov. 18, 2019.
Dermlite Website, "DL Connection Kit for iPhone 7 Plus & 8 Plus," https://dermlite.com/collections/connection-kits/products/dermlite-connection-kit-iphone-7-plus, site visited Nov. 18, 2019.
Dermlite Website, "DL Connection Kit for iPhone 7 & 8," https://dermlite.com/collections/connection-kits/products/dl-connection-kit-for-iphone-7-8, site visited Nov. 18, 2019.
Dermlite Website, "DL Connection Kit for iPhone 6/6S Plus," https://dermlite.com/collections/connection-kits/products/dermlite-connection-kit-for-iphone-6-plus, site visited Nov. 18, 2019.
Dermlite Website, "DL Connection Kit for iPhone 6/6S," https://dermlite.com/collections/connection-kits/products/dermlite-connection-kit-for-iphone-6, site visited Nov. 18, 2019.
Dermlite Website, "DL Connection Kit for iPhone 5/5S/SE," https://dermlite.com/collections/connection-kits/products/dermlite-connection-kit-for-iphone-5s, site visited Nov. 18, 2019.
Dermlite Website, "DL Connection Kit for iPhone 5C," https://dermlite.com/collections/connection-kits/products/dermlite-connection-kit-for-iphone-5, site visited Nov. 18, 2019.
Dermlite Website, "DL Connection Kit for iPhone 4/4S," https://dermlite.com/collections/connection-kits/products/dermlite-connection-kit-for-iphone-4-4s, site visited Nov. 18, 2019.
Dermlite Website, "DL Connection Kit for iPad Pro 10.5 & iPad Air 3," https://dermlite.com/collections/connection-kits/products/dl-connection-kit-for-ipad-pro-10-6, site visited Nov. 18, 2019.
Dermlite Website, "DL Connection Kit for iPad Pro 9.7," https://dermlite.com/collections/connection-kits/products/dermlite-ipad-pro-9-7-connection-kit, site visited Nov. 18, 2019.
Dermlite Website, "DL Connection Kit for iPad 5 & 6," https://dermlite.com/collections/connection-kits/products/dermlite-connection-kit-for-ipad-5, site visited Nov. 18, 2019.
Dermlite Website, "DL Connection Kit for iPad 3 & 4," https://dermlite.com/collections/connection-kits/products/dermlite-connection-kit-for-ipad-3-4, site visited Nov. 18, 2019.
Dermlite Website, "DL Connection Kit for iPad Air 2," https://dermlite.com/collections/connection-kits/products/dermlite-connection-kit-for-ipad-air-2, site visited Nov. 18, 2019.
Dermlite Website, "DL Connection Kit for iPad mini 4," https://dermlite.com/collections/connection-kits/products/ipad-mini-4th-gen, site visited Nov. 18, 2019.
Dermlite website, "DL Connection Kit for iPad Mini (1-3)," https://dermlite.com/collections/connection-kits/products/connection-kit-for-ipad-mini, Retrieved Nov. 18, 2019.
Dermlite website, "DL Connection Kit for Galaxy S8+," https://dermlite.com/collections/connection-kits/products/dermlite-connection-kit-for-galaxy-s8-1, Retrieved Nov. 18, 2019.
Dermlite website, "DL Connection Kit for Galaxy S8," https://dermlite.com/collections/connection-kits/products/dermlite-connection-kit-for-galaxy-s8, Retrieved Nov. 18, 2019.
Dermlite website, "DL Connection Kit for Galaxy S7," https://dermlite.com/collections/connection-kits/products/dermlite-connection-kit-for-galaxy-g7, Retrieved Nov. 18, 2019.
Dermlite website, "DL Connection Kit for Galaxy S6," https://dermlite.com/collections/connection-kits/products/dermlite-connection-kit-for-galaxy-s6, Retrieved Nov. 18, 2019.
Dermlite website, "DL Connection Kit for Galaxy S5," https://dermlite.com/collections/connection-kits/products/dermlite-connection-kit-for-galaxy-s5, Retrieved Nov. 18, 2019.
Dermlite website, "DL Connection Kit for Galaxy S4," https://dermlite.com/collections/connection-kits/products/dermlite-connection-kit-for-galaxy-s4, Retrieved Nov. 18, 2019.
Dermlite website, "DL Connection Kit for Galaxy S3," https://dermlite.com/collections/connection-kits/products/dermlite-connection-kit-for-galaxy-s3, Retrieved Nov. 18, 2019.
Dermlite website, "DL Connection Kit for iPod Touch 5/6/7th Generation," https://dermlite.com/collections/connection-kits/products/dermlite-connection-kit-for-ipod-touch-6th-generation, Retrieved Nov. 18, 2019.

* cited by examiner

MEDICAL ILLUMINATOR MOBILE DEVICE ATTACHMENT APPARATUS AND METHOD

CROSS-REFERENCE TO RELATED APPLICATIONS

This application is a continuation-in-part of and claims priority to U.S. application Ser. No. 16/261,239, filed Jan. 29, 2019, now issued as U.S. Pat. No. 10,678,120 on Jun. 9, 2020, the entire contents of which are hereby fully incorporated herein by reference for all purposes.

STATEMENT RE: FEDERALLY SPONSORED RESEARCH/DEVELOPMENT

Not Applicable

BACKGROUND

Technical Field

The present inventive subject matter relates generally to an attachment mechanism and method for interfacing a hand-held illumination device used in medical examinations to a mobile device camera. More particularly, the inventive subject matter relates to an improved apparatus and method for attaching dermatoscopes to mobile devices using a magnetic array of alternately polarized magnet elements to provide a minimized magnetic field and also increasing the attraction strength for a more secure attachment of a dermatoscope to a mobile device.

Background

Medical examinations by physicians may employ the use of hand held illuminators to assist the doctor in magnified and non-magnified viewing of the tissue of a patient. Hand held illuminators may include pen lights, which are widely used by general medical practitioners. Also, physicians and medical practitioners make use of hand-held illumination devices that have magnification lenses including otoscopes, ophthalmoscopes and dermatoscopes. Otoscopes, ophthalmoscope and dermatoscopes typically include lighting and magnification and are designed for particular types of examination.

In dermoscopy, dermatology and medical practices that examine features of the human skin, hand-held dermoscopy devices are used that deploy light with magnification. Dermoscopy devices are shown and described in U.S. Pat. No. 7,006,223 issued on Feb. 28, 2006 to Mullani, and U.S. Pat. No. 7,167,243 issued Jan. 23, 2007 to Mullani, the substance of each of which is wholly incorporated herein by reference. Dermatoscopes also are described in U.S. Pat. No. 7,027,153 issued on Apr. 11, 2006 to Mullani and U.S. Pat. No. 7,167,244 issued on Jan. 23, 2007 to Mullani, the substance of each of which is wholly incorporated herein by reference. In addition, a dermoscopy device is described in U.S. Pat. No. 9,458,990 issued on Oct. 4, 2016 to Mullani, the substance of which is wholly incorporated herein by reference.

Many medical optical devices, such as the dermatoscopes described in the patents identified in the preceding paragraphs, are analog in nature and designed for the medical practitioner to view the magnified images using the human eye. Such dermatoscope devices do not have internal image capture mechanism to record electronic images of the magnified illuminated skin area. As such, by interfacing the lens of a dermatoscope to the camera lens of a mobile device such as a mobile phone or tablet, the user can either record the image by saving the magnified image to a memory, or view the lesion on the mobile device screen. Viewing on the mobile device screen can be used for inspection of the skin or lesion rather than an analog viewing of skin without the aid of a camera or screen, or as a compliment to viewing the same with the human eye. For example, a medical practitioner may identify lesions or other items of interest on the skin of a patient. If a lesion or item of interest warrants electronic capture, the practitioner can to attach the analog dermatoscope to a readily available mobile phone or other electronic device having a camera to capture the image through the lens of a dermatoscope.

Known devices provide mechanical interfaces for attaching dermatoscopes or other medical examination devices with lenses to mobile devices for the purpose of using a mobile device camera to capture images from the lens of a dermatoscope or other device. For example, connection kits may include a cell phone cover that has at least one magnet formed around a camera area. A steel or metal member or a plurality of series of steel or metal members may be provided to encircle the lens of a dermatoscope, or one or more steel members may be formed into the dermatoscope or other medical device. The steel members of the dermatoscopes or medical device mate with one or more magnets on the mobile device cover to cause the camera of the mobile device to connect with and be in alignment with the lens of the dermatoscope. One such device is known as the DL™ Connection Kit sold by 3Gen, Inc. of San Juan Capistrano, Calif. Also, dermatoscopes may include threads that are designed to interface with a camera, much like a camera lens. In this regard, 3Gen, Inc. of San Juan Capistrano, Calif. also provides its MagnetiConnect® device consisting of a magnet assembly that is mechanically connected to a cell phone case and a steel ring that can be engaged with existing threads surrounding the dermatoscope lens to provide a metal mating surface for the magnet assembly.

Magnets positioned in a mobile device case or attached to the mobile device used for interconnecting to a corresponding metal interface on a medical examination device such as a dermatoscope will generate static magnetic fields. Many hospitals and health care providers recognize that magnetic fields are a form of electromagnetic interference (EMI) that have the possibility of affecting sensitive medical equipment. As such, while magnetic coupling devices are useful in interconnecting mobile device cameras to medical examination optical devices such as dermatoscopes, it would be advantageous to minimize the magnetic fields of magnets used for the couplers. As such there is a need to provide medical device couplers used with mobile device camera lenses that have reduced magnetic fields and avoid unnecessary EMI in the medical setting.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

BRIEF SUMMARY

The inventive subject matter described herein demonstrates a device and method for interfacing a mobile device camera and a medical illuminator to be used in medical examinations.

The described device may be used to capture electronic images of the magnified illuminated skin area by interfacing the lens of a dermatoscope or other optical device to the camera lens of a mobile device such as cell phone. For example, a medical practitioner may identify lesions or other items of interest on the skin of a patient. If a lesion or item of interest warrants electronic capture, the practitioner can use the device and method disclosed herein to attach the analog dermatoscope to a readily available mobile phone or another electronic device having a camera to capture the image through the lens of a dermatoscope. Electronic devices with cameras may include mobile phones, phablets, tablets, PDAs or other similar devices.

The disclosure herein demonstrates an attachment apparatus for optically coupling a mobile device camera to a lens of a medical examination device. The device incudes an attachment body, the proximal side of which attaches to a mobile device or to a mobile device cover. The proximal side of the attachment body includes an array of magnets that comprises at least one pair of axially magnetized magnets, wherein the pair of axially magnetized magnets are positioned in antiparallel arrangement relative to each other. On the distal side of the attachment device, an array of magnets are provided that are positioned radially around an aperture wherein at least one pair of axially magnetized magnets are positioned in antiparallel arrangement relative to each other. It is understood that axially magnetized magnets positioned in antiparallel relation reduce the expanse of a magnetic field while at the same time increasing the magnetic field strength close to the magnetic poles. Reducing EMI emanating from magnetic connectors may be important in settings that require, mandate or suggest that EMI be reduced, such as in a medical setting to help in avoiding interference with medical devices.

The devices described herein are capable of coupling to a medical examination device such as a dermatoscope for example, and incorporate at least one ferromagnetic metal element capable of magnetically coupling with said pair of axially magnetized magnets. A ferromagnetic metal element may be formed surrounding a lens of a medical examination device for magnetically coupling the aperture of said attachment body in alignment with said lens.

Also discussed and disclosed is a method for optically coupling a mobile device camera to a lens of a medical examination device by positioning an array of magnets on a mobile device in a radial configuration around an aperture and also positioning at least one pair of axially magnetized magnets in antiparallel arrangement to each other in the array of magnet. A further step comprises coupling said array of magnets to at least one ferromagnetic metal element formed around a lens of a medical examination device such as a dermatoscope, for example. The magnets may also be diametrically magnetized magnets.

Also disclosed herein is an attachment apparatus for optically coupling a mobile device camera to a lens of a medical optical device wherein an array of magnets radially positioned around a mobile device camera lens, said array of magnets comprising axially magnetized magnets positioned in antiparallel mode relative to each other.

Also disclosed is an attachment apparatus for optically coupling a camera to a lens of an optical device having an array of magnets radially positioned around a camera lens, said array of magnets comprising axially magnetized magnets positioned in antiparallel mode relative to each other in alternating polarity. As is further disclosed, an attachment apparatus for optically coupling a camera to a lens of an optical device which includes an array of axially magnetized magnets radially positioned around a camera lens, said array of magnets comprising at least one pair of axially magnetized magnets positioned in parallel polarity relative to each other.

Also disclosed is a further embodiment of an attachment apparatus using an axially magnetized circular magnet positioned with an annular recess formed in an annular steel member, wherein the opposite side of the annular steel member is attached around a camera lens of a mobile device. It is understood that the axially magnetized circular magnet positioned within a steel casing on three sides, creates a pot magnet effect that reduces the expanse of a magnetic field while at the same time increasing the magnetic field strength close to the exposed surface of the axially magnetized steel magnet.

Also disclosed is an attachment apparatus for optically coupling a mobile device camera to a lens of an medical optical device, the apparatus having a body with a proximal side and a distal side, the proximal side having a first array of magnets which are releasably detachable from the body, and which can be reversibly positioned on the body at a first position and a second position to accommodate differently positioned lenses for different mobile devices. Said first array of magnets comprising axially magnetized magnets positioned in antiparallel mode relative to each other in alternating polarity. The first array of magnets may be positioned radially around an aperture wherein each axially polarized magnet is positioned in antiparallel arrangement relative to each adjacent axially magnetized magnet. The distal side of the body having a second array of magnets, said array of magnets comprising at least one pair of axially magnetized magnets positioned in parallel polarity relative to each other.

Also disclosed is an attachment apparatus for optically coupling a mobile device camera to a lens of an medical optical device, the apparatus having a body with a proximal side and a distal side, the proximal side having a first array of magnets which are slidably positioned on the body at a first position and a second position to accommodate differently located lenses for different mobile devices. Said first array of magnets comprising axially magnetized magnets positioned in antiparallel mode relative to each other in alternating polarity. The first array of magnets may be positioned radially around an aperture wherein each axially polarized magnet is positioned in antiparallel arrangement relative to each adjacent axially magnetized magnet. The distal side of the body having a second array of magnets, said array of magnets comprising at least one pair of axially magnetized magnets positioned in parallel polarity relative to each other.

Also disclosed is an attachment apparatus for optically coupling a mobile device camera to a lens of a medical optical device, the apparatus having a body with a proximal side and a distal side, the proximal side having a first magnetic array of two intersected circular magnetic arrangements for positioning the attachment body at first and second distances. The arrays comprise axially magnetized magnets positioned in antiparallel mode relative to each other in alternating polarity. The distal side of the body having a second array of magnets, said array of magnets comprising at least one pair of axially magnetized magnets positioned in parallel polarity relative to each other.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
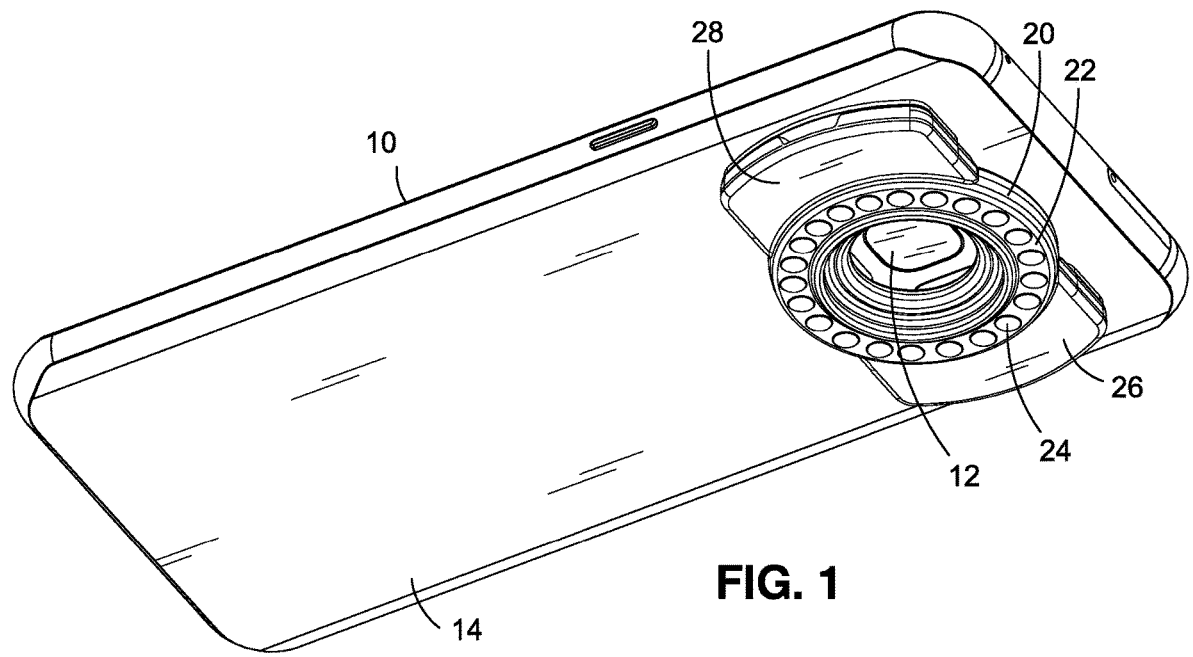
FIG. 1 is a view of the disclosed attachment device attached to a mobile device.

The detailed description set forth below in connection with the appended drawings is intended as a description of certain embodiments of an attachment apparatus and method and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

The background, summary and the above description includes information that may be useful in understanding the present disclosure. It is not an admission that any of the information provided herein is prior art or relevant to the presently claimed inventive subject matter, or that any publication specifically or implicitly referenced is prior art.

In some embodiments, the numbers expressing dimensions, quantities, quantiles of ingredients, properties of materials, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclose may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the disclosure and does not pose a limitation on the scope of the claimed inventive subject matter. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Various objects, features, aspects and advantages of the inventive subject matter will become more apparent from the following detailed description of preferred embodiments, along with the accompanying drawing figures in which like numerals represent like components.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

With regard to FIGS. 1-3, 21-25 there is shown an embodiment of the connector device disclosed herein. Referring particularly to FIG. 1, there is shown a mobile device 10, wherein a camera lens 12 is positioned on the distal side 14 of the mobile device 10. For purposes of this description, the distal side 14 of the mobile device 10 is the side opposite of the screen of a mobile device such as a mobile phone or tablet. In the configuration of the mobile device 10 shown in FIG. 1, a camera lens 12 is positioned on or near the vertical centerline on the distal side 14 of the mobile device 10. The side of the mobile device 10 having a screen 16 and typically facing the user for purposes of this disclosure will be referred to as the proximal side 18 of the mobile device 10.

The connector device 20 as shown in FIG. 1 includes an annular carrier 22 for holding a plurality of magnets 24. The carrier 22 is integrated with connector wings 26 and 28 that hold, as described in more detail herein with regard to FIG. 2, the connector device 20 in contact with the mobile device 10. The magnets 24 which are described in greater detail herein with regard to FIG. 21-25 are axially polarized magnets and are placed in the carrier 22 in a particular pattern of alternating polarity. The alternating polarity provides less stray EMI and creates a greater field strength close to the magnets. The magnet arrangement as described in FIGS. 21-25 maintains and/or increases the near field forces while reducing the far field forces that may interfere with EMI sensitive equipment or devices, such as equipment and devices found in medical settings. In addition, it is contemplated by this disclosure that the axially polarized magnets can be placed in parallel polarity. In addition, it is contemplated by this disclosure that diametrically magnetized magnets can be employed in the various embodiments disclosed herein as such diametrically magnetized magnets are capable of being placed in both antiparallel and parallel arrangements.

Figure 2:
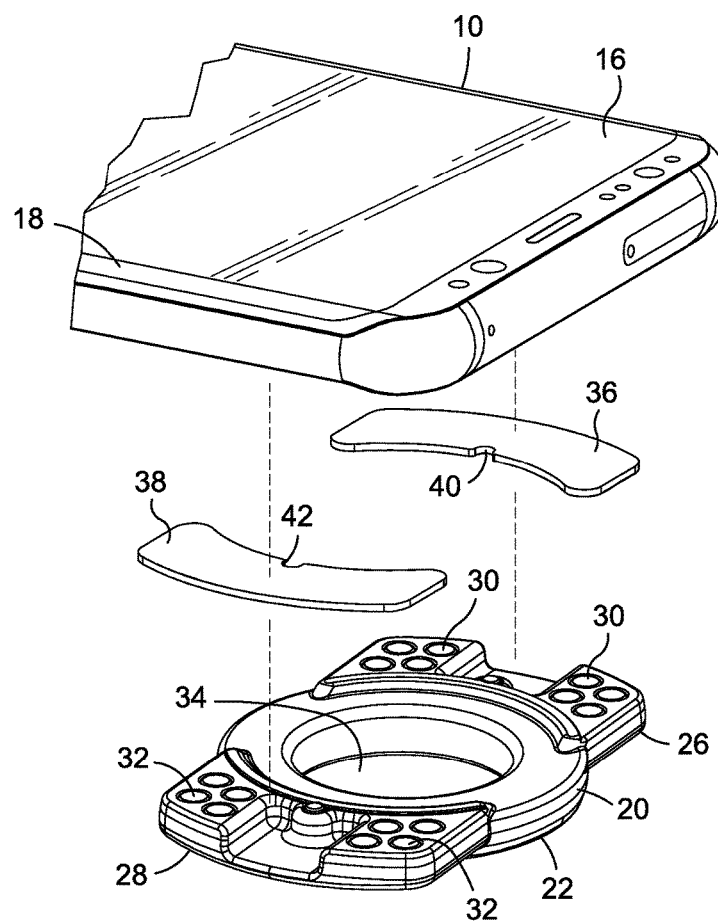
FIG. 2 is an exploded view of the disclosed attachment device separated from a mobile device and a pair of metal elements that interface between the mobile device and the attachment device.

Referring particularly FIG. 2, there is shown an exploded view of the connector device 20, having the center annular carrier 22 and connector wings 26 and 28. The annular carrier 22 forms an aperture 34 that aligns with a lens 12 (not shown) when connected to a mobile device 10. In FIG. 2, the exploded view shows the rear side of the connector device 20 that includes a plurality of axially polarized magnets 30 and 32. The magnets 30 and 32 are described in greater detail herein with regard to FIG. 21-25 wherein the magnets 30 and 32 are placed into recesses formed in the rear of the connector wings 26 and 28 in a particular pattern of alternating polarity which can also be described as each magnet being positioned in antiparallel relation to each adjacent magnet, creating less EMI and increasing field strength close to the magnets. The antiparallel magnet arrangement maintains the near field forces while reducing the far field forces that may interfere with EMI sensitive equipment or devices, such as equipment and devices found in medical settings. Generally planar steel elements 38 and 36 are affixed to the distal side 14 of the mobile device 10. The steel elements 36 and 38 include alignment notches 40 and 42 and the steel elements 36 and 38 are affixed to the distal side 14 of the mobile device 10 by an adhesive to surround the camera 12 (not shown) to provide a ferromagnetic interface so that the magnets 30 and 32 of the connector device 20 couple to the distal side 14 of the mobile device 10. As such, when coupled to the distal side 14 of the mobile device 10 to the steel elements 36 and 38, the aperture 34 of the connector device 20 is alignment with the lens 12. While the steel elements 36 and 38 are connected to mobile device 10, it is contemplated that steel elements 36 and 38 can be affixed to a cell phone case by an adhesive or other method of attachment, or the steel elements 36 and 38 could be formed into a cell phone case or embedded directly into the mobile device. In the embodiment of FIGS. 21-25 and other embodiments deploying axially magnetized magnets positioned in antiparallel relation, it is understood that the shown pattern of magnets could be all be reversed in polarity (i.e. the opposite pattern) so as to maintain the antiparallel relation between the magnets to achieve the same effect.

Figure 3:
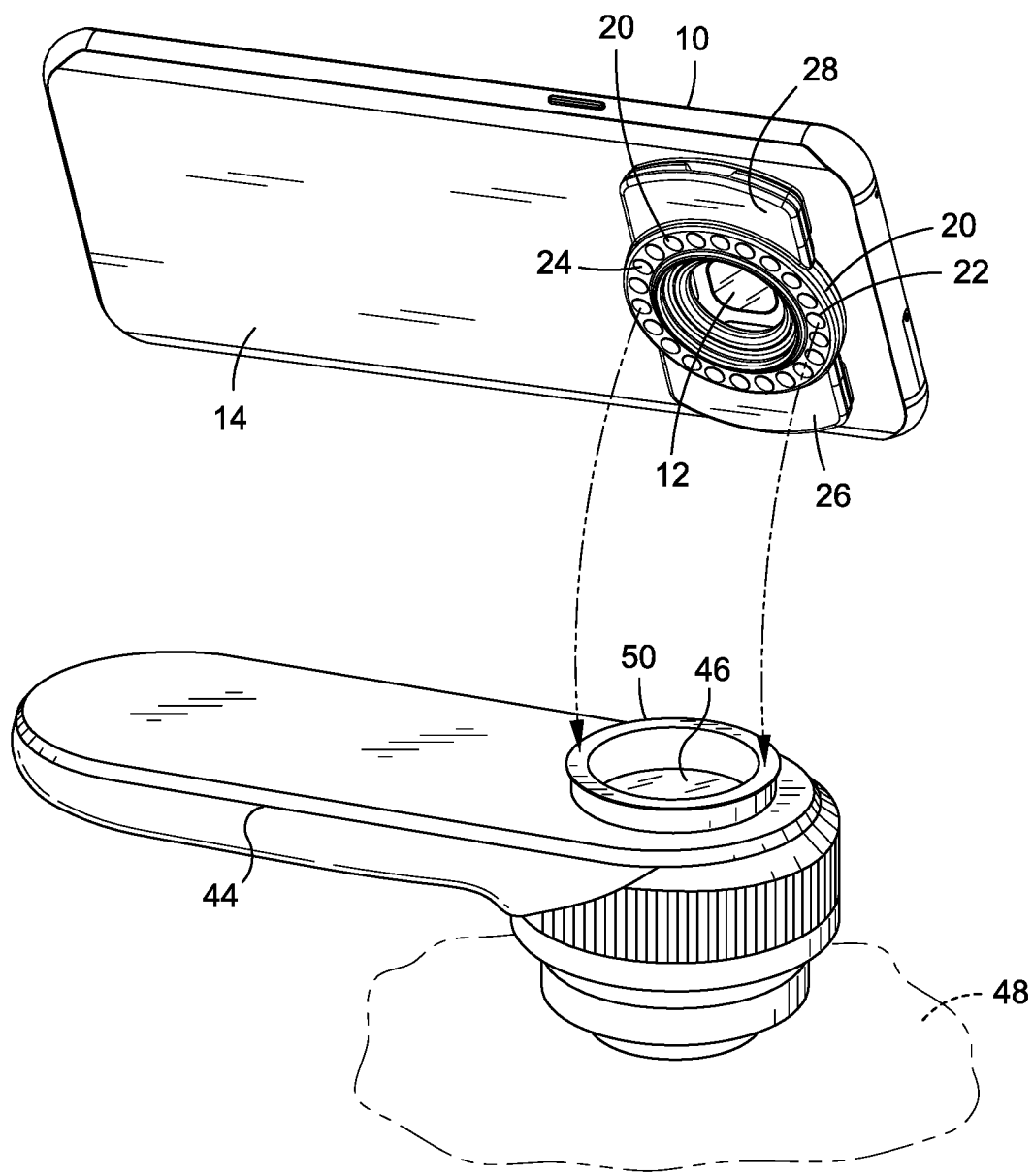
FIG. 3 is a view of the attachment device attached to a mobile device, with lead lines showing how the magnetic array interfaces with a metal ring formed about the lens of a dermatoscope.

Referring particularly to FIG. 3, the connector device 20 is shown coupled to the mobile device 10. A dermatoscope 44 is shown, with an eyepiece lens 46. In analog use of the dermatoscope 44 a medical practitioner looks through the lens 46 to observe an object 48, such as a patient's skin. In operation, using the connector device 20 to interface between the mobile device 10 and the dermatoscope 44, a user couples the connector device 20 using the magnets 24 formed in the annular carrier 22 to mate with steel a ring 50 formed around the eyepiece lens 46 so that the lens 12 of the mobile device 10 is in alignment with the lens 46. In this way, the lens 12 of the mobile device 10 captures an image through the dermatoscope lens 46 of an object 48. This allows the user to store images from the dermatoscope 44 into the memory of the mobile device 10, or otherwise, can view any object 48 on the mobile device 10 via screen 16 (not shown).

Figure 4:
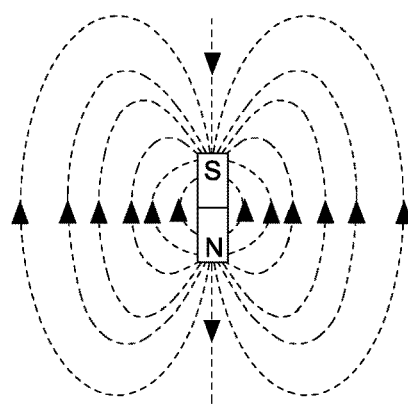
FIG. 4 is a schematic view of an axially magnetized magnet with representation of magnetic flux.
Figure 5:
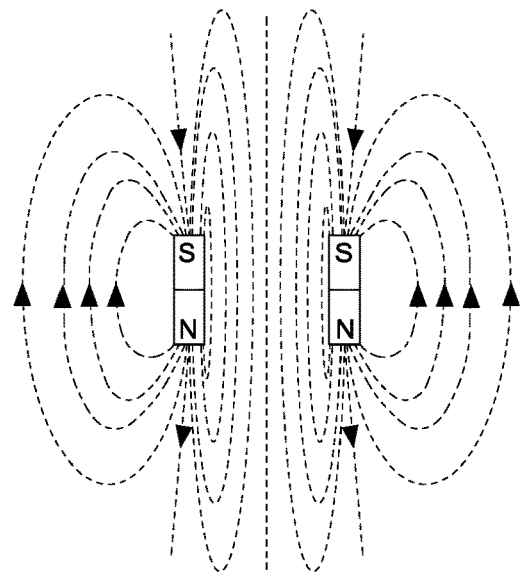
FIG. 5 is a schematic view of a pair of axially magnetized magnets position in parallel relation with representation of magnetic flux.

As disclosed in the various embodiments described herein, axially polarized magnets are placed in patterns of alternating polarity. For purposes of this this disclosure the terms "axially polarized" and "axially magnetized" are used interchangeably. The effects and behaviors of the axially polarized magnets used in different configurations are discussed herein including the effects upon EMI and magnetic field flux strength. For example, referring particularly to FIG. 4, there is shown graphical representations of magnetic field lines of a single bar magnet that is axially magnetized. Magnetic field density, or a stronger field (higher Gauss) collects around the magnetic poles. The magnetic field is modified when a second bar magnet which is axially magnetized is introduced into proximity of the first bar magnet, as shown in FIG. 5. As shown in FIG. 5 the second bar magnet is placed in parallel relationship, where the like magnetic poles face the same direction. In the graphical representation of FIG. 5, the magnetic field is demonstrated to increase covering a larger area in space and the field strength near the magnet poles increases. As such, this parallel relationship of like polarity increases the magnetic field.

Figure 6:
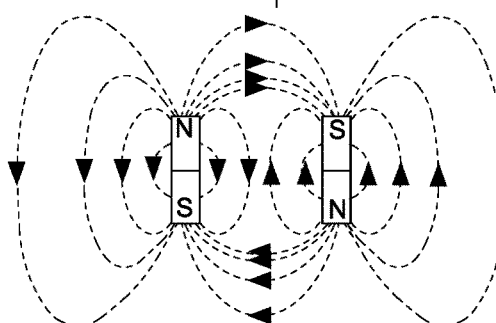
FIG. 6 is a schematic view of a pair of axially magnetized magnets positioned in antiparallel relation with representation of magnetic flux.
Figure 7:
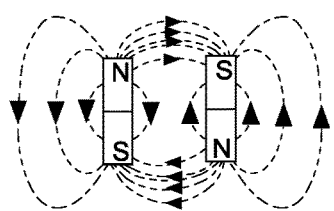
FIG. 7 is a schematic view of a pair of axially magnetized magnets positioned in antiparallel relation in closer proximal range than FIG. 6 with representation of magnetic flux.
Figure 8:
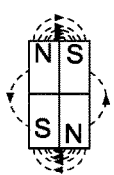
FIG. 8 is a schematic view of a pair of axially magnetized magnets positioned in antiparallel relation in contact relation with representation of magnetic flux.

A different result is achieved if the axially magnetized bar magnets are placed in antiparallel relationship as shown in FIG. 6. For purposes of this disclosure, antiparallel relationship or antiparallel mode means that a pair of axially magnetized magnets are places in opposite polarity arrangement (each is placed in reverse polarity to the other). This arrangement, as shown in FIG. 6 reduces the field size, but increases the field strength between the oppositely positioned and opposite polarity poles. FIG. 7 provides a graphical representation of the same antiparallel relationship between to axially magnetized bar magnets where the magnets are moved closer together. In the arrangement of FIG. 7 compared to FIG. 6, field size continues to decrease, but the field strength adjacent the magnetic poles increases. Lastly in FIG. 8, the antiparallel axially magnetized bar magnets are placed in contact relation demonstrating a significant reduced field size, but a further increased field strength directly adjacent the magnetic poles.

A comparison of magnet types demonstrates the effectiveness of the antiparallel magnet configurations deployed by the various embodiments as disclosed herein. Referring particularly to FIG. 9-20 there is shown magnetostatic simulations of various magnet configurations that can be used in connectors around an eyepiece and lens. The graphics of FIGS. 11, 14, 17 and 20 plot the magnetic flux density readings (i.e. Gauss) in the surrounding air space of a centered cross section of a magnet or magnet assembly. Each chart shown in FIGS. 11, 14, 17 and 20 are scaled identically, each having a 20 mm×20 mm grid overlaid for reference.

Figure 9:
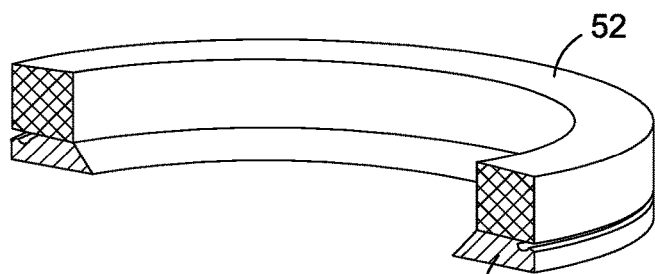
FIG. 9 is a cross sectional view of axially magnetized annular magnet.
Figure 10:
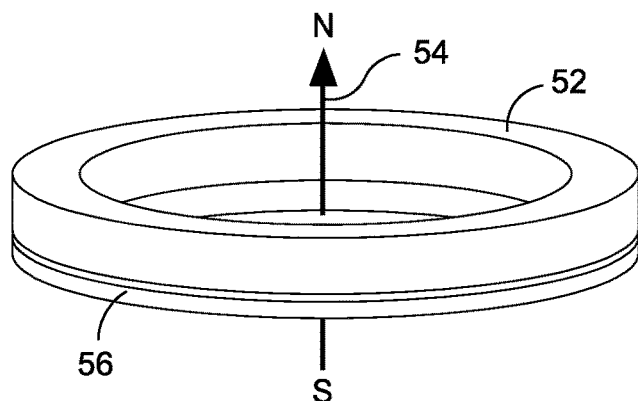
FIG. 10 is a view of an axially magnetized annular magnet.
Figure 11:
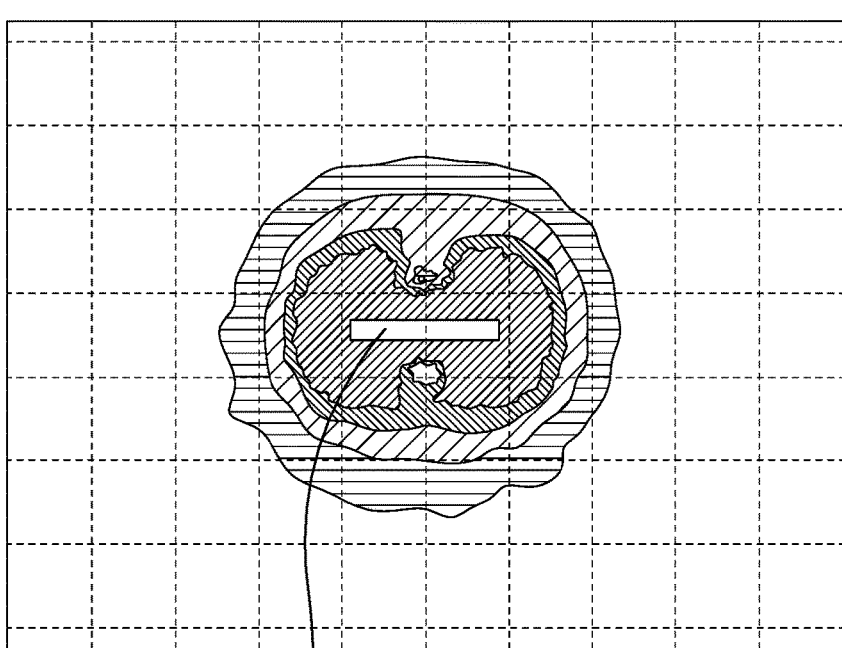
FIG. 11 is a graphical view of magnetic flux density values of the annular magnet of FIGS. 9 and 10.

Referring particularly to FIG. 9-11 there is shown an axially magnetized ring magnet 52. The arrow 54 in FIG. 10 demonstrates axial magnetization. FIG. 9 shows a cross section of ring magnet 52. The ring magnet 52 is magnetically coupled to an annular steel plate 56. In operation the ring magnet 52 is connected to a mobile device and provides the coupling force to attach to the steel plate 56 formed around the eyepiece lens of a dermatoscope. The magnetic ring 52 coupled to the annular steel plate 56 is simulated in FIG. 11 to show the magnetic field. A combined cross section 58 of the magnetic ring 52 and steel plate 56 is shown at the center of the simulation in FIG. 11. As can be appreciated the 22 Gauss magnetic flux density extends significantly far from the combined cross section 58.

Figure 12:
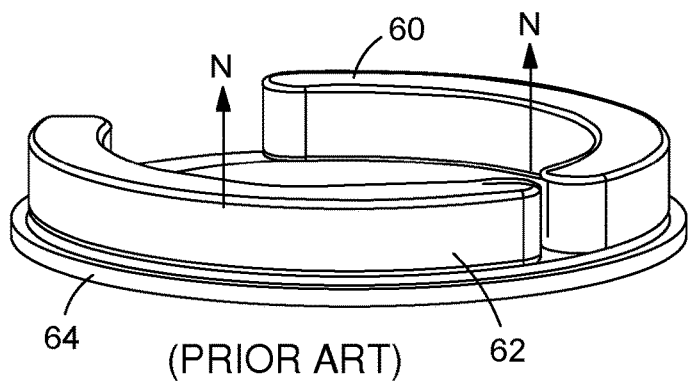
FIG. 12 is a view of two axially magnetized semi-circular magnets positioned an annular arrangement.
Figure 13:
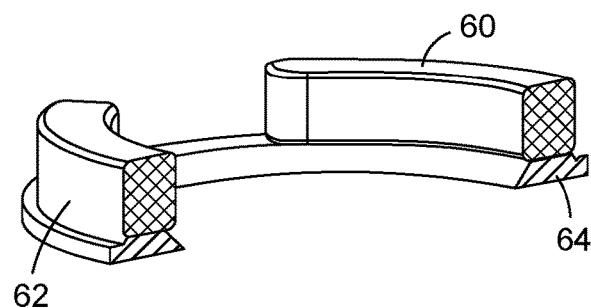
FIG. 13 is a cross sectional view of two axially magnetized semi-circular magnets of FIG. 12.
Figure 14:
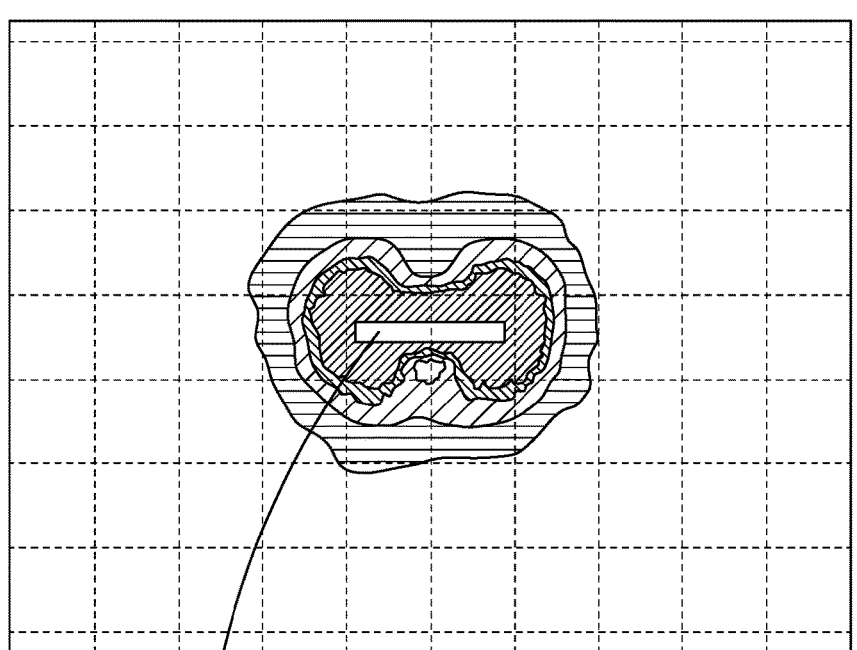
FIG. 14 is a graphical view of magnetic flux density values of the annular magnet of FIGS. 12 and 13.

Referring particularly to FIG. 12-14 there is shown a pair of axially magnetized c-shaped magnets 60 and 62. The arrows in FIG. 12 show the north south direction of axial magnetization. FIG. 13 shows a cross sections of c-shaped magnets 60 and 62. The c-shaped magnets 60 and 62 are magnetically coupled to an annular steel plate 64. In operation the c-shaped magnets 60 and 62 are connected to a mobile device and provide the coupling force to attach to the steel plate 64 formed around the eyepiece lens of a dermatoscope. The c-shaped magnets 60 and 62 coupled to the annular steel plate 64 is simulated in FIG. 14 to show the magnetic field. A combined cross section 66 of the c-shaped magnets 60 and 62 coupled to the annular steel plate 64 is shown at the center of the simulation FIG. 14. As can be appreciated the 22 Gauss magnetic flux density extends significantly far from the combined cross section 66, and it is estimated that flux density of over 4 Gauss at distances 58 mm from the combined magnets and steel plate 66.

Figure 15:
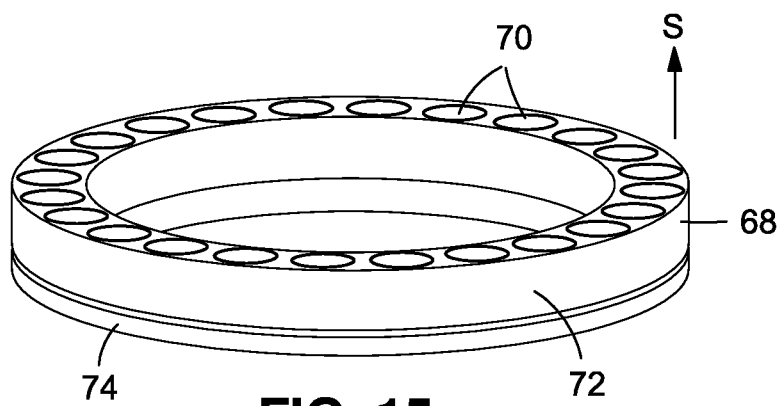
FIG. 15 is a view of an array of axially magnetized magnets formed into an annular base with the magnets positioned in magnetic parallel.
Figure 16:
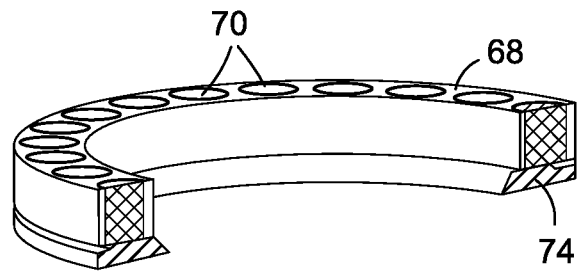
FIG. 16 is a cross sectional view of the magnetic array of FIG. 15.
Figure 17:
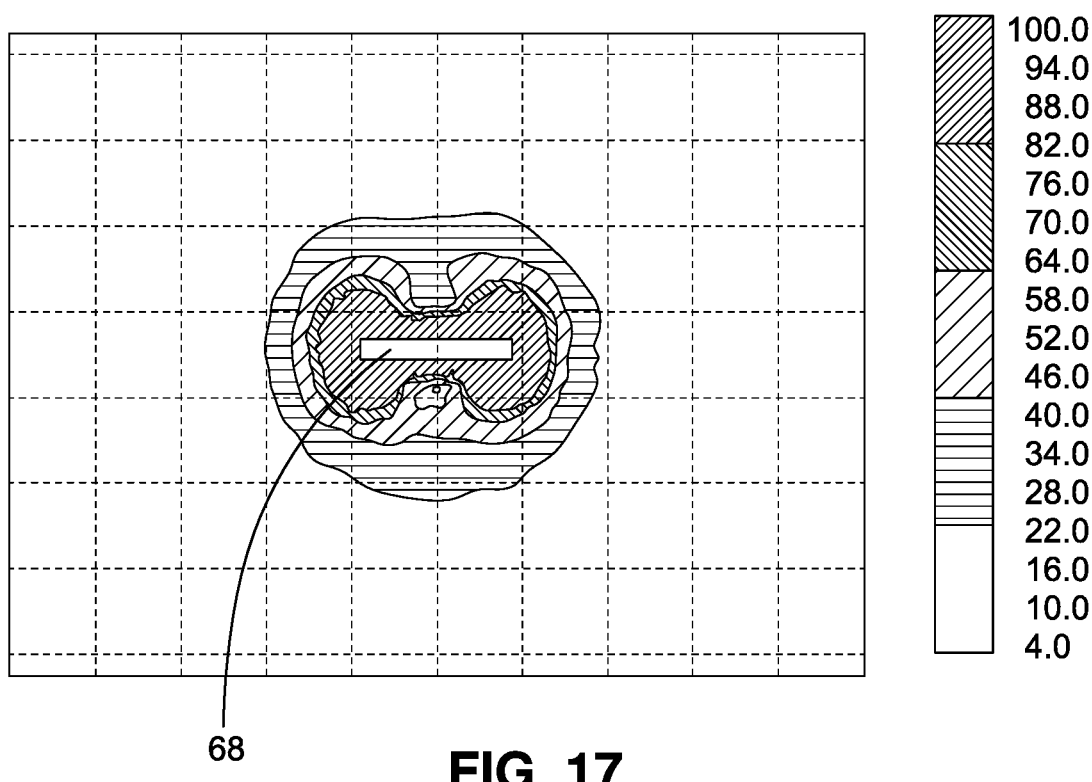
FIG. 17 is a graphical view of magnetic flux density values of the annular magnet array of FIGS. 15 and 16.

Referring particularly to FIG. 15-17 there is shown a magnetic array 68 of twenty-four (24) axially magnetized magnets 70 positioned in an annular carrier 72. The annular carrier 72 is formed from a non-ferromagnetic substance, such as plastic or aluminum, that does not significantly interact with the magnetic field. The arrow in FIG. 15 show the north south orientation of axial magnetization of the magnets 70. Each of the magnets 70 are positioned in the same orientation, ie. with all south poles facing upward. FIG. 16 shows a cross section of the magnetic array 68. The magnetic array 68 is magnetically coupled to an annular steel plate 74. In operation, the magnet array 68 may be connected to a mobile device and provides the coupling force to attach to the steel plate 74 formed around the eyepiece lens of a dermatoscope. The magnetic array 68 coupled to the annular steel plate 74 is simulated in FIG. 17. A combined cross section 76 of the magnetic array 68 coupled to the annular steel plate 74 is shown at the center of the simulation FIG. 17. As can be appreciated the magnetic flux density is generally consistent with the simulation described in FIG. 14.

Figure 18:
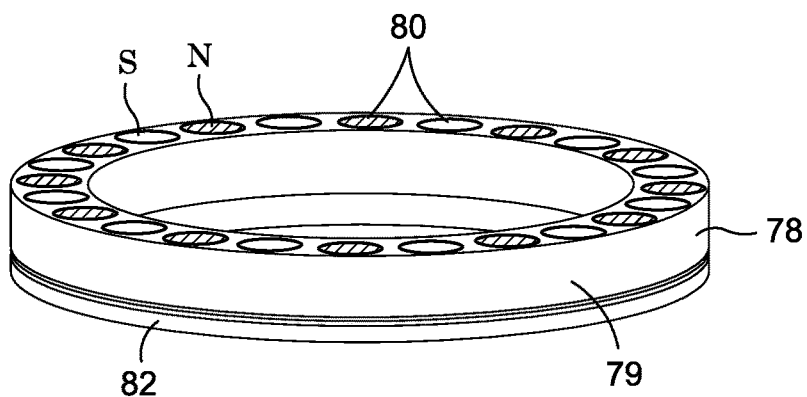
FIG. 18 is a view of an array of axially magnetized magnets formed into an annular base with the magnets positioned in antiparallel magnetic relation.
Figure 19:
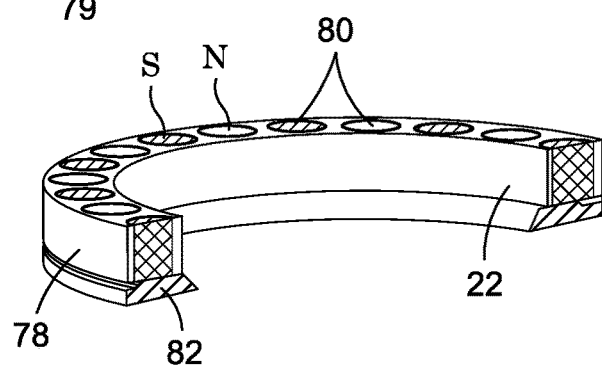
FIG. 19 is a cross sectional view of the magnetic array of FIG. 18.
Figure 20:
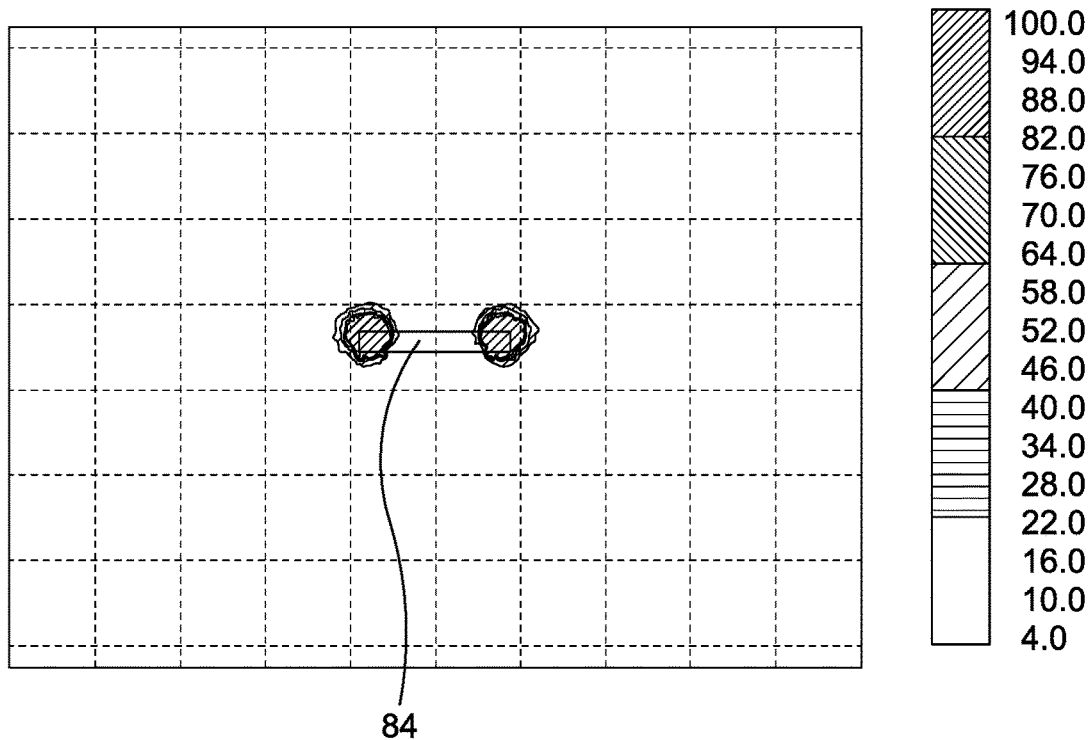
FIG. 20 is a graphical view of magnetic flux density values of the annular magnet array of FIGS. 18 and 19.

Referring particularly to FIG. 18-20 there is shown a magnetic array 78 of twenty-four (24) axially magnetized magnets 80 positioned in an annular carrier 79. The annular carrier 79 is formed from a non-ferromagnetic or non-metallic substance, such as plastic, that does not significantly interact with the magnetic field. Each of the axially magnetized magnets 80 are positioned in antiparallel relation to an adjacent magnet. As shown in FIGS. 18 and 19, the hatched magnets 80 show north pole of the magnet facing upward and the magnets 80 without the hatching show the south pole of the magnet facing upward. FIG. 19 shows a cross section of the magnetic array 78. The magnetic array 78 is magnetically coupled to an annular steel plate 82. In operation, the magnetic array 78 may be connected to a mobile device and provides the coupling force to attach to the steel plate 82 formed around the eyepiece lens of a dermatoscope. The magnetic array 78 coupled to the annular steel plate 82 is simulated in FIG. 17 to show magnetic field. A combined cross section 84 of the magnetic array 78 coupled to the annular steel plate 82 is shown at the center of the simulation FIG. 20. As can be appreciated from the graphics, the magnetic flux density is significantly reduced in area surrounding the cross section 84.

Figure 21:
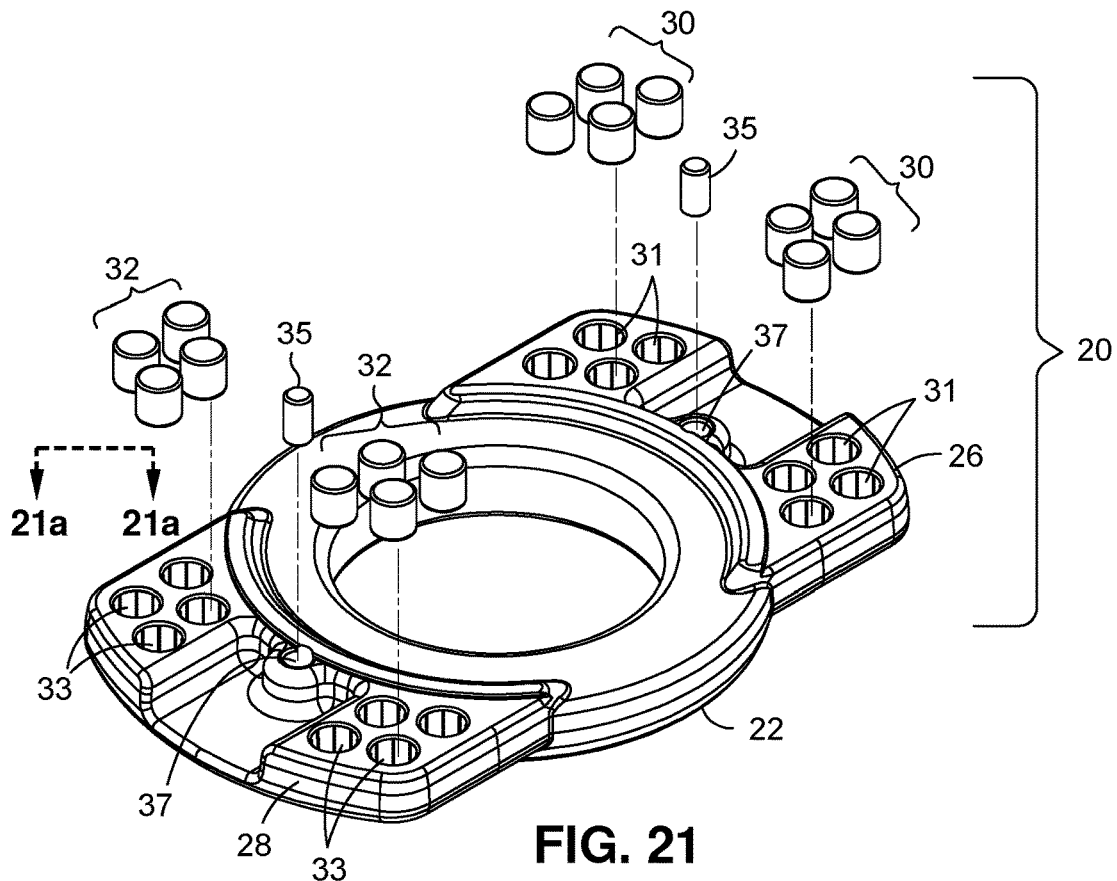
FIG. 21 is a view of the proximal side of the attachment device of FIG. 1-3, showing the axial magnetized magnets and pins exploded from the device.
Figure 22:
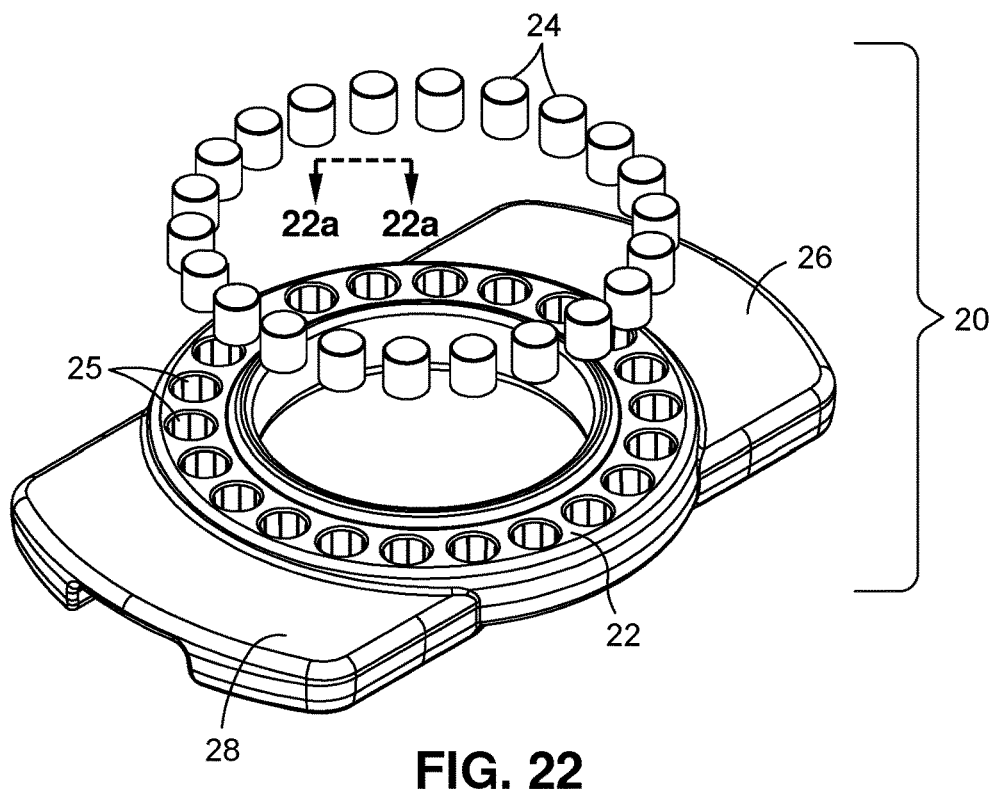
FIG. 22 is a view of the distal side of the attachment device of FIGS. 1-3 and 21, showing the axial magnetized magnets exploded from the device.
Figure 21A:
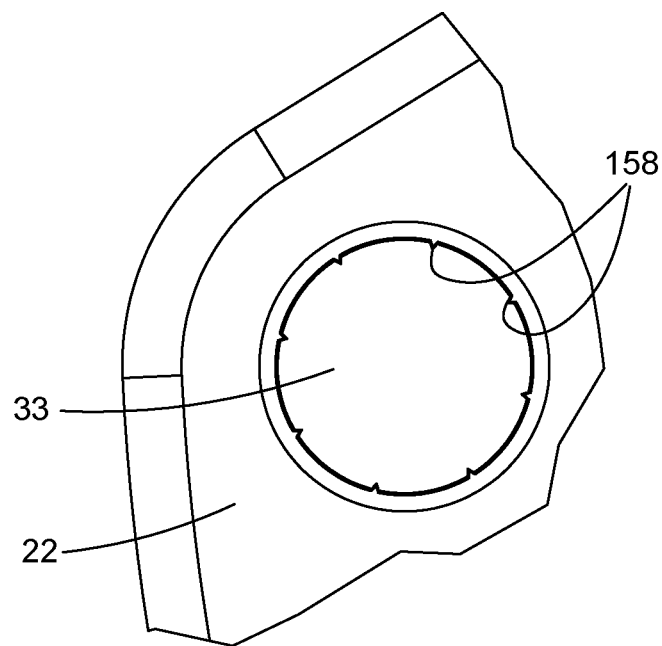
FIG. 21a is an enlarged view of recess 33 of FIG. 21.
Figure 22A:
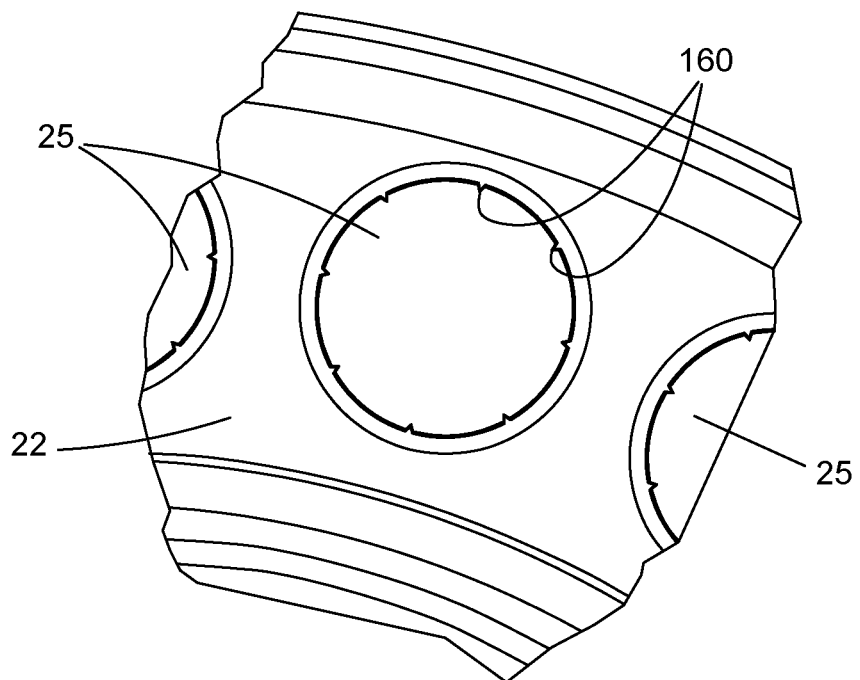
FIG. 22a is an enlarged view of recess 25 of FIG. 22.

Referring particularly to FIGS. 21-25, there is shown the embodiment also shown in FIGS. 1-3. FIG. 21 shows the proximal side of the connector device 20, with magnets 30 and 32 exploded from the connector wings 26 and 28. Magnets 30 and 32 are rare earth magnets and may comprise neodymium, N42 grade ⅛ inch by ⅛-inch magnet with nickel plating. As shown, the magnets are cylindrical shaped. The magnets 30 and 32 are axially magnetized along the length of the cylinder shape with the poles having flat ends. Each of the magnets have corresponding recesses 31 and 33 formed in the connector wings 26 and 28. Magnets 30 and 32 are pressed into place into recesses 31 and 33 for an interference fit, such the magnets 30,32 are fixed in place into the recesses 31,33. The connector device 20 may be formed of injection molded polycarbonate material. As such, as shown in FIG. 21*a*, crush rib features 158 are molded within recesses 31 and 33. These crush ribs 158 deform as the magnets 30 and 32 are pressed into place to account for diametrical manufacturing tolerances of both the magnets and recesses. The crush ribs 158 also avoid subjecting the brittle magnets to exceedingly high compressive forces that may damage the magnets. Structures identical to crush ribs 158 can be found in recesses of other embodiments described herein, for example as shown in FIGS. 22 and 22*a*

Figure 28:
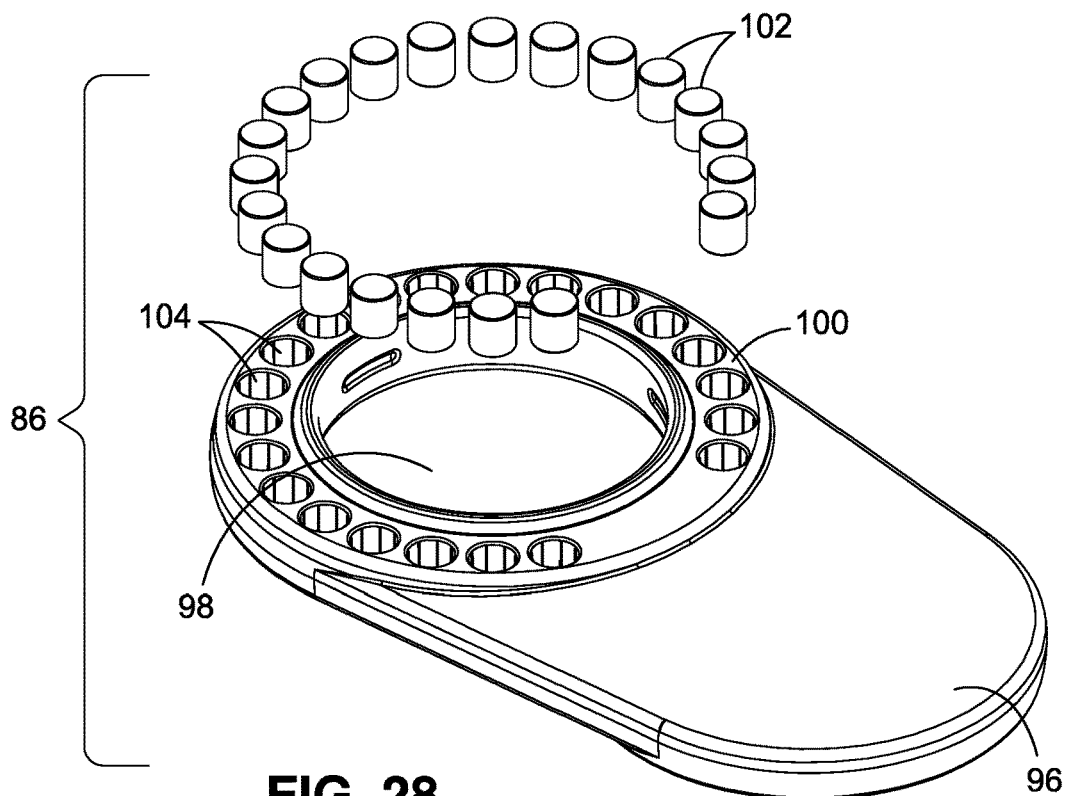
FIG. 28 is a view of the distal side of the device of the embodiment of FIG. 26-27 with the axial magnetized magnets exploded from the device.
Figure 29:
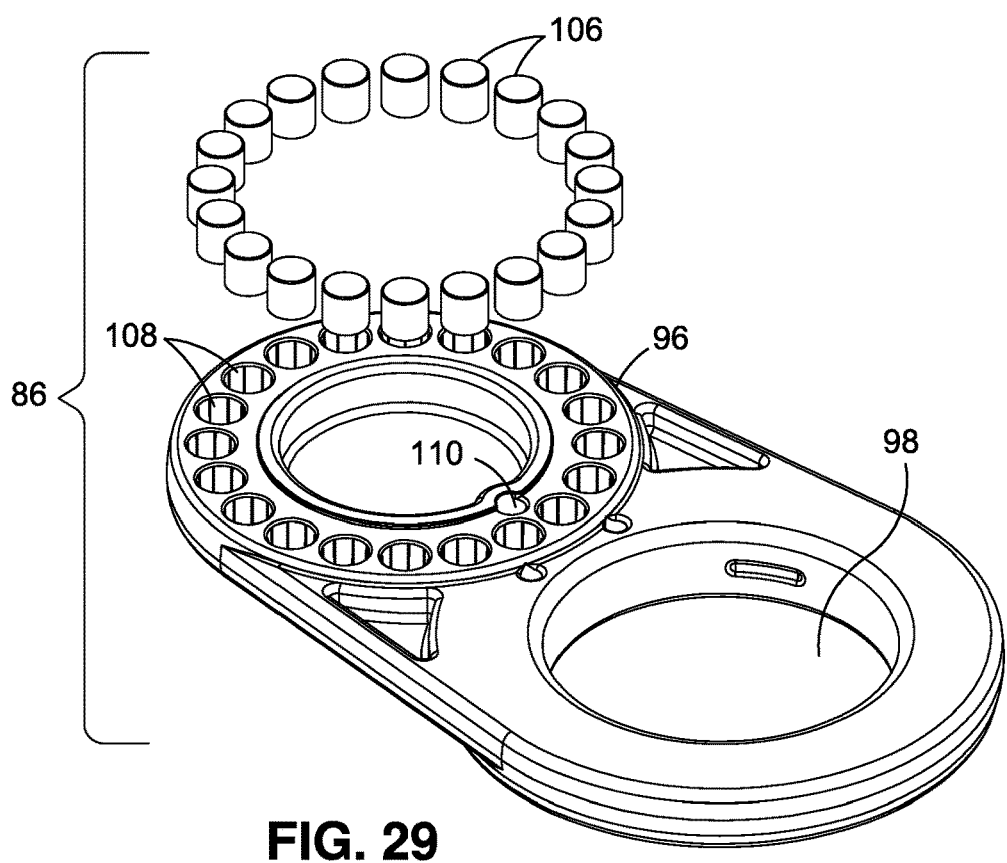
FIG. 29 is a view of the proximal side of the device of the embodiment of FIGS. 26-28 with the axial magnetized magnets exploded from the device.

(recesses 25), FIG. 28 (recesses 104) and FIG. 29 (recesses 108). The interconnecting components of the device 20, in this embodiment and each of the embodiments described herein, are formed of assembled pieces of injection molded polycarbonate. It will be recognized by one skilled in the art that interconnecting components of the device 20 can be formed of other suitable rigid lightweight material, including, but not limited to plastic, composite materials, fiberglass, aluminum, PVC, acetate and/or lexan. It will also be recognized by one skill in the art that the magnets may be attached by other suitable means including, but not limited to bonding in place with adhesives, insert molded, and mechanical restraint.

Figure 24:
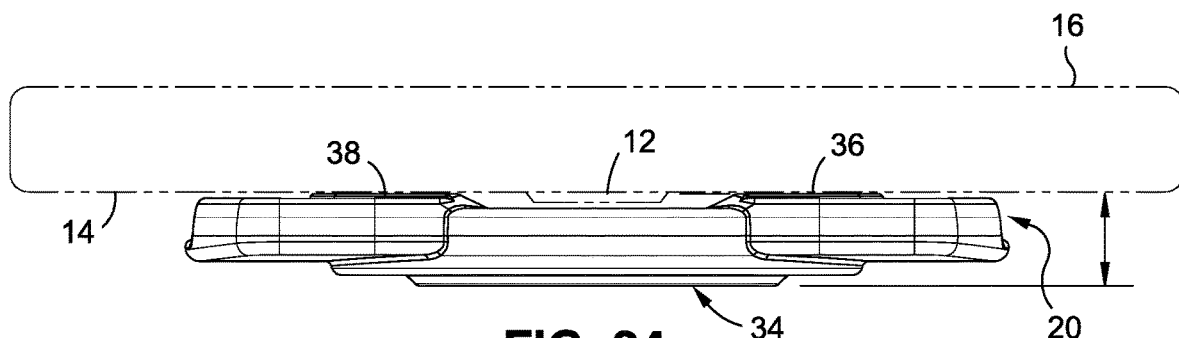
FIG. 24 is a side view of the attachment device of FIGS. 1-3 and 21-23 showing attachment to a mobile device.
Figure 25:
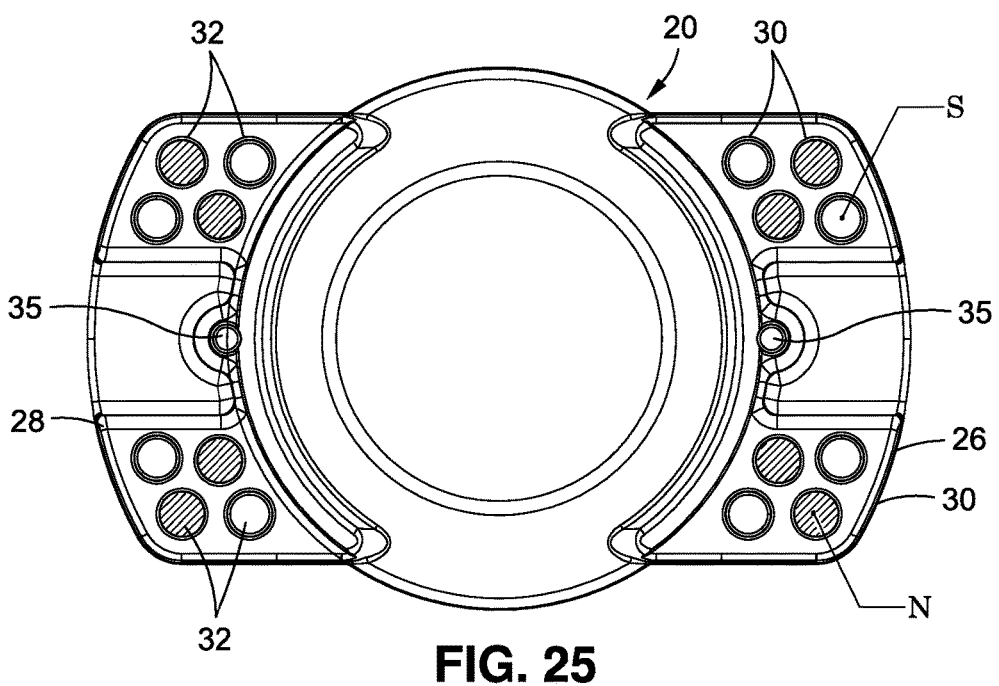
FIG. 25 is a plan view of the proximal side of the attachment device of FIGS. 1-3, and 21-24 with polarity of the magnets indicated.

As described with regard to FIG. 2, and also referring to FIG. 24, the magnets 30,32 are designed to couple to metal elements 36, 38 fixed or formed on the distal side 14 of a mobile device 10 to hold the entire connector device 20 onto the mobile device 10 to align the mobile device camera lens 12 with the aperture 34 formed in the connector device 20. As shown in FIG. 25 the magnets 30,32 are positioned in wings 26, 28 in alternating polarity which can also be described as each magnet being positioned in antiparallel to adjacent magnets. In FIG. 25 the hatched magnets 30, 32 represent magnets with the north polarity facing the proximal side of the connector device 20, while magnets 30,32 not being hatched in the drawing represent magnets with the south polarity facing the proximal side of the connector device 20. As described herein the alternating polarity magnets reduce EMI by reducing magnetic flux around the connector device 20, while increasing the magnetic flux strength close to the magnet poles. The antiparallel magnet arrangement maintains the near field forces while reducing the far field forces that may interfere with EMI sensitive equipment or devices, such as equipment and devices found in medical settings.

FIG. 21 also shows pins 35 that fit into pin recesses 37. Referring also to FIG. 2, the pins 35 are positioned to interface with alignment notches 40, 42 formed in metal elements 36, 38. As such, the cooperation of the pins 35 with notches 40, 42 keep the connector 20 in alignment on the distal side 14 of the mobile device 10.

Figure 23:
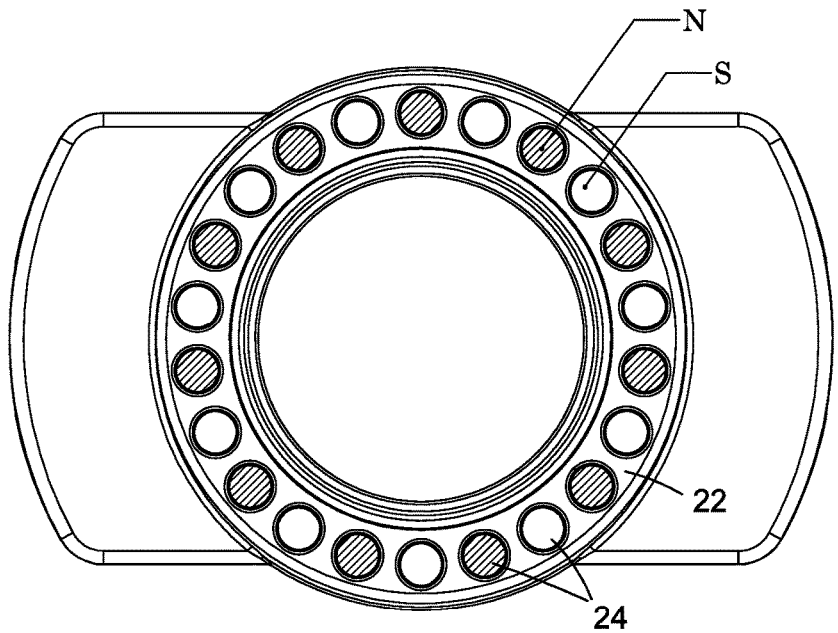
FIG. 23 is a plan view of the distal side of the attachment device of FIGS. 1-3 and 21-22 with polarity of the magnets indicated.

FIG. 22 shows the distal side of the connector device 20, with magnets 24 exploded from the annular carrier 22. The annular carrier is formed of substance, such as plastic, that does not significantly interact with the magnets 24. Magnets 24 may be identical to the magnets 30 and 32 and are rare earth magnets and may comprise neodymium, N42 grade ⅛ inch by ⅛-inch magnet with nickel plating. As shown, the magnets are cylindrical shaped. The magnets 24 are axially magnetized along the length of the cylinder shape with the poles having flat ends. Each of the magnets have corresponding recesses 25 with crush ribs 160 formed in the connector annular carrier 22 as shown in FIG. 22a. Magnets 24 are pressed into place into recesses 25 for an interference fit, such the magnets 24 are fixed in place into the recesses 25. As described with regard to FIG. 3, the magnets 24 are designed to couple to one or more metal elements fixed or formed around the eyepiece lens of a dermatoscope device to hold the entire connector device 20, along with a mobile device 10 onto a dermatoscope to align the mobile device camera lens 12 with eyepiece lens of a dermatoscope. As shown in FIG. 23 the magnets 24 are positioned in the annular carrier 22 in alternating polarity which can also be described as each magnet being positioned in antiparallel relation to each adjacent magnet. In FIG. 23 the hatched magnets 24 represent magnets with the north polarity facing the distal side of the connector device 20, while magnets 24 not being hatched in the drawing represent magnets with the south polarity facing the distal side of the connector device 20. As described herein the alternating polarity magnets reduce EMI by reducing magnetic flux around the connector device 20, while increasing the magnetic flux strength close to the magnet poles. The antiparallel magnet arrangement maintains the near field forces while reducing the far field forces that may interfere with EMI sensitive equipment or devices, such as equipment and devices found in medical settings.

Figure 26:
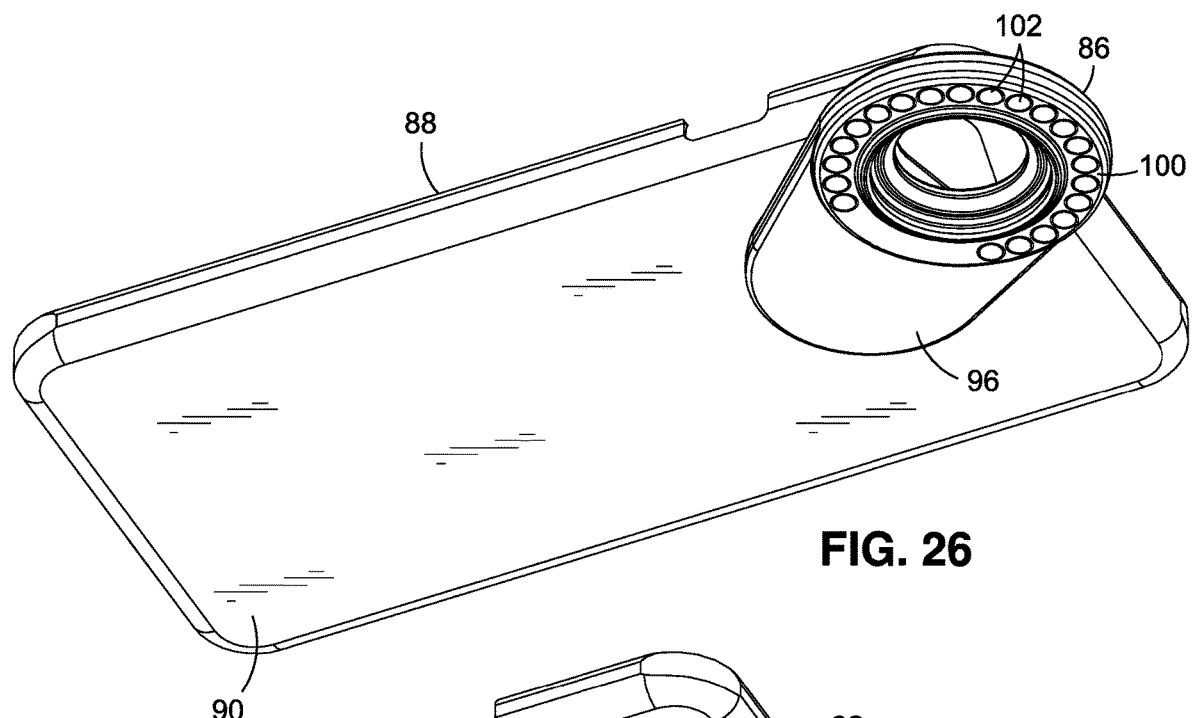
FIG. 26 is a view of an alternative embodiment of the disclosed attachment device, showing the device attached to a mobile device case.
Figure 27:
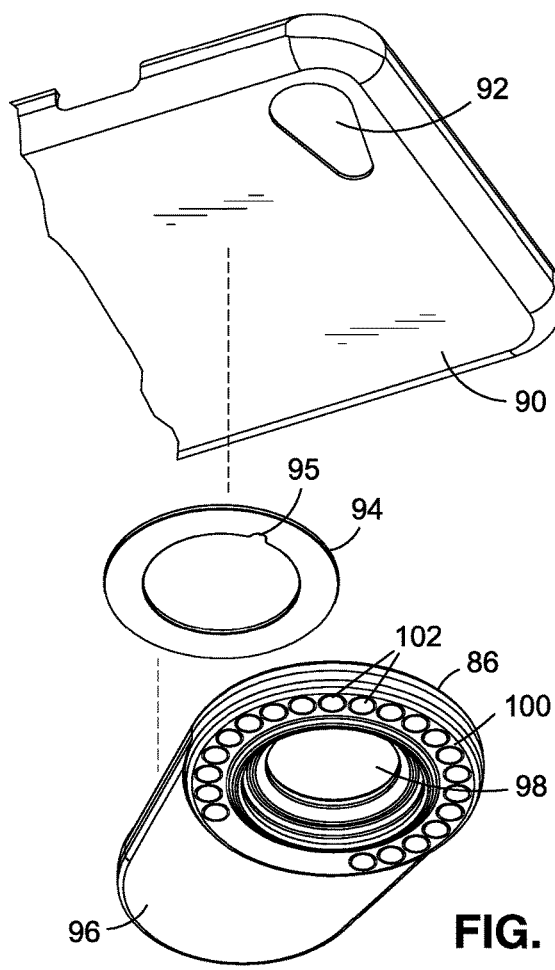
FIG. 27 is an exploded view of the embodiment attachment device of FIG. 26 separated from a mobile device and an annular metal element that interfaces between the mobile device and the attachment device.

FIGS. 26-30 show the configuration of a further embodiment of a connector device 86 used for interconnecting a mobile device to a dermatoscope or other optical device. Referring particularly to FIG. 26, there is shown connector device 86 engaged with a cell phone case 88. In particular, the device 86 is interfaced with the distal side 90 of the cell phone case 88. Cell phone case 88 is designed to be used with mobile device products with a camera opening 92 formed in the upper corner of the cell case 88 to conform to the electronic device. As such the connector 86 is designed to accommodate the corner positioning of camera opening 92. FIG. 27 shows an exploded view of FIG. 26 showing a steel or metal annular ring 94 that attaches by adhesive or other attachment means to the distal side 90 of the cell case 88. Magnets (not shown) formed on the proximal side of the wing 96 of connector device 86 magnetically couple to the ring 94 to hold the connector device 86 onto the cell case 88, with the camera opening 92 in alignment with the aperture 98 of the connector device 86. While the ring 94 can be attached by adhesive, the ring can 94 can also be integrally formed in or on the cell case 88. A magnetic array carrier 100 includes a plurality of magnets 102 positioned on the distal side of the connector device 86 to provide magnetic coupling interface for a steel or metal ring that is formed around the eyepiece of a dermatoscope device for example as shown in FIG. 3. The connector device 86 may be formed of injection molded polycarbonate material or other suitable rigid material.

Figure 30:
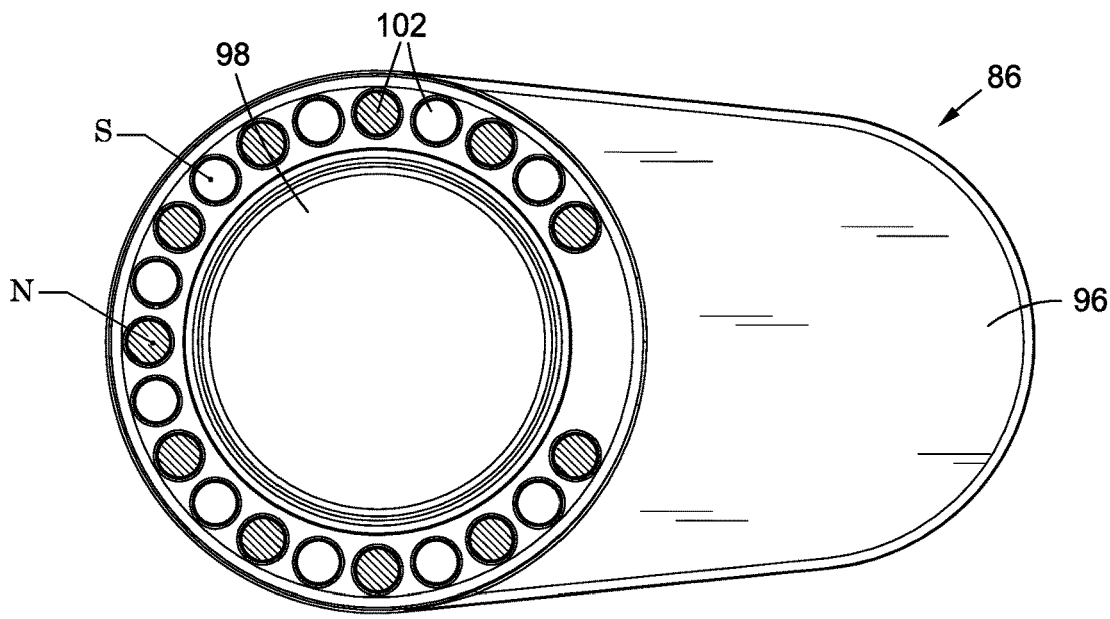
FIG. 30 is a plan view of the distal side of the device of the embodiment of FIGS. 26-29 showing the polarity of the magnets.

FIG. 28 shows the distal side of the connector device 86, with magnets 102 exploded from the annular carrier 100. Magnets 102 are rare earth magnets and may comprise neodymium, N42 grade ⅛ inch by ⅛-inch magnet with nickel plating. As shown, the magnets are cylindrical shaped. The magnets 102 are axially magnetized along the length of the cylinder shape with the poles having flat ends. Each of the magnets have corresponding recesses 104 with crush ribs formed in the connector annular carrier 100. Magnets 102 are pressed into place into recesses 104 for an interference fit, such the magnets 102 are fixed in place into the recesses 104. As described with regard to FIG. 3, the magnets 102 are designed to couple to one or more metal elements fixed or formed around the eyepiece lens of a dermatoscope device to hold the entire connector device 86, along with a mobile device nested into the cell case 88 onto a dermatoscope to align the mobile device camera lens through camera opening 92 with eyepiece lens of a dermatoscope. As shown in FIG. 30 the magnets 102 are positioned in the annular carrier 100 in alternating polarity which can also be described as each magnet being positioned in antiparallel relation to each adjacent magnet. In FIG. 30 the hatched magnets 102 represent magnets with the north polarity facing the distal side of the connector device 86, while magnets 102 not being hatched in the drawing represent magnets with the south polarity facing the distal side of the connector device 86. As described herein the alternating polarity magnets reduce EMI by reducing magnetic flux around the connector device 86, while increasing the magnetic flux strength close to the magnet poles. The antiparallel magnet arrangement maintains the near field forces while reducing the far field forces that may interfere with EMI sensitive equipment or devices, such as equipment and devices found in medical settings. This disclosure also contemplates that the magnets 102 may be positioned in parallel polarity.

FIG. 29 shows the proximal side of the connector device 86, with magnets 106 exploded from the wing 96. Magnets 106 are rare earth magnets and may comprise neodymium, N42 grade ⅛ inch by ⅛-inch magnet with nickel plating. As shown, the magnets are cylindrical shaped. The magnets 106 are axially magnetized along the length of the cylinder shape with the poles having flat ends. Each of the magnets 106 have corresponding recesses 108 with crush ribs formed in the connector wing 96 in circular arrangement. Magnets 106 are pressed into place into recesses 108 for an interference fit, such the magnets 106 are fixed in place into the recesses 108. The connector device 20 may be formed of injection molded polycarbonate material or other suitable material.

Figure 31:
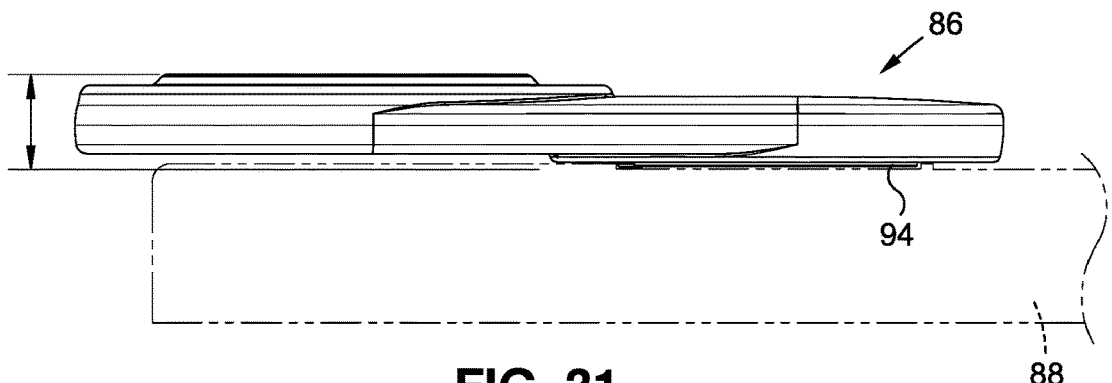
FIG. 31 is a side view of the device of the embodiment of FIGS. 26-30 attached to a mobile device case.
Figure 32:
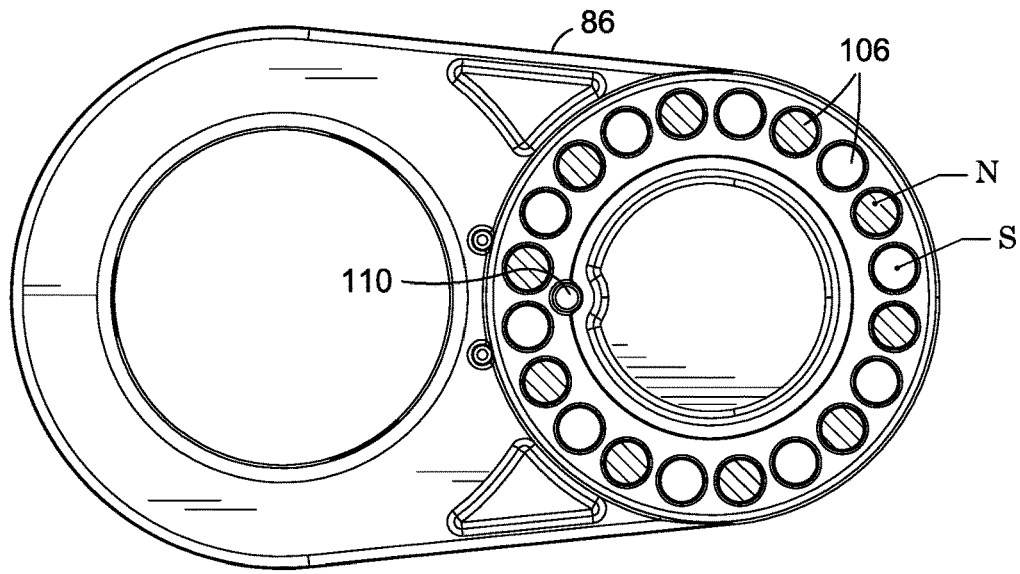
FIG. 32 is a plan view of the proximal side of the device of the embodiment of FIGS. 26-31 showing the polarity of the magnets.

Referring to FIG. 32, the magnets 106 are designed to couple to metal element 94 fixed or formed on the distal side 90 of a mobile device case 88 to hold the entire connector device 86 onto the mobile device case 88, so that when a mobile device is nested into the mobile device case 88, a mobile device camera lens aligns through opening 92 of the case 88 with the aperture 98 formed in the connector device 86. As shown in FIG. 32 the magnets 106 are positioned in wing 96 in alternating polarity which can also be described as each magnet being positioned in antiparallel relation to adjacent magnets. In FIG. 32 the hatched magnets 106 represent magnets with the north polarity facing the proximal side of the connector device 86, while magnets 106 not being hatched in the drawing represent magnets with the south polarity facing the proximal side of the connector device 86. As described herein the alternating polarity magnets reduce EMI by reducing magnetic flux around the connector device 86, while increasing the magnetic flux strength close to the magnet poles. The antiparallel magnet arrangement maintains the near field forces while reducing the far field forces that may interfere with EMI sensitive equipment or devices, such as equipment and devices found in medical settings. This disclosure also contemplates that the magnets 106 may be positioned in parallel polarity. Also referring to FIG. 31, the magnets 106 are designed to couple to metal elements 94 fixed or formed on the distal side 90 of a mobile device case 88 to hold the entire connector device 86 onto the mobile device case 88 to align a mobile device camera lens through the camera opening 92 with the aperture 98 formed in the connector device 86.

Referring to FIGS. 27, 29, 31 and 32 metal ring 94 includes an alignment notch 95, that allows a pin (not shown) formed in pin recess 110 to cooperate with the notch 95. As such, the cooperation of a pin (not shown) that interfaces with pin recess 110 and notch 95 keeps the connector 86 in alignment on the distal side 90 of the mobile device case 88.

Figure 33:
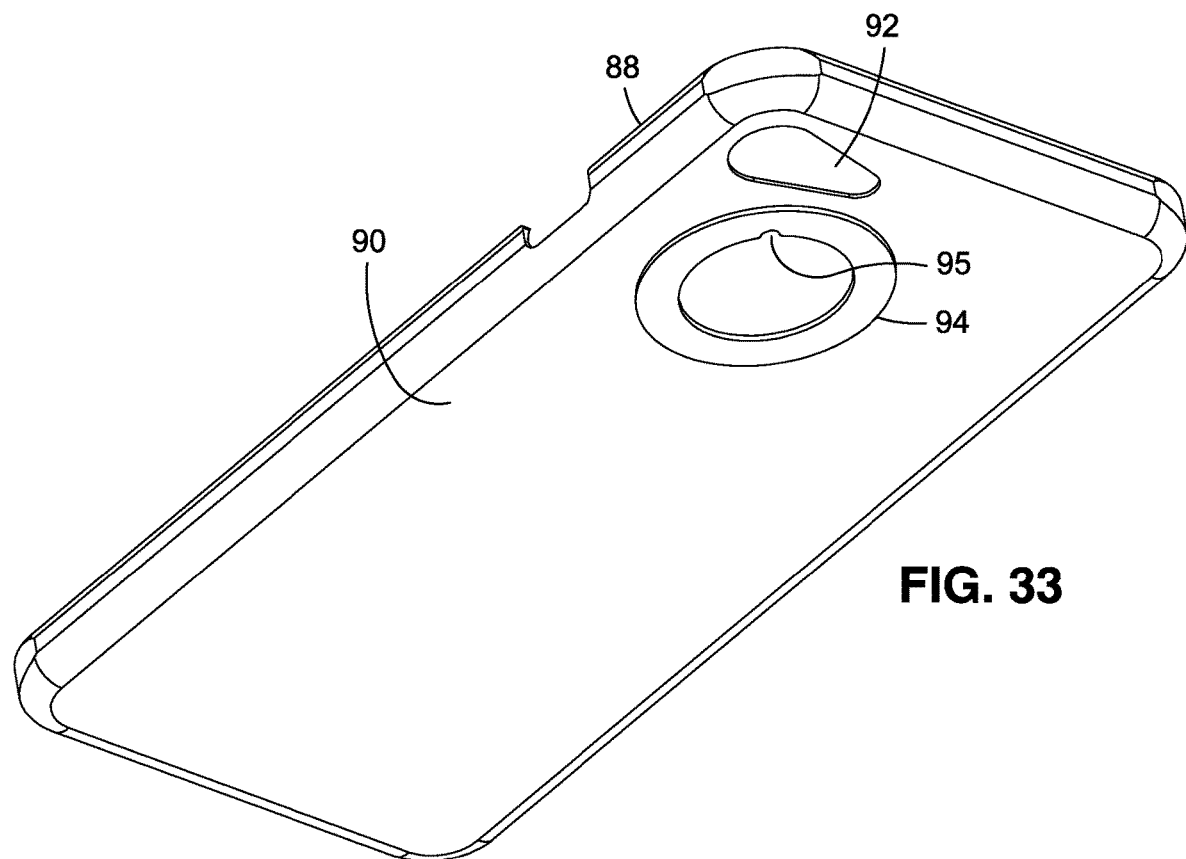
FIG. 33 is a view of a mobile device case with an annular metal member attached to the mobile device case.
Figure 34:
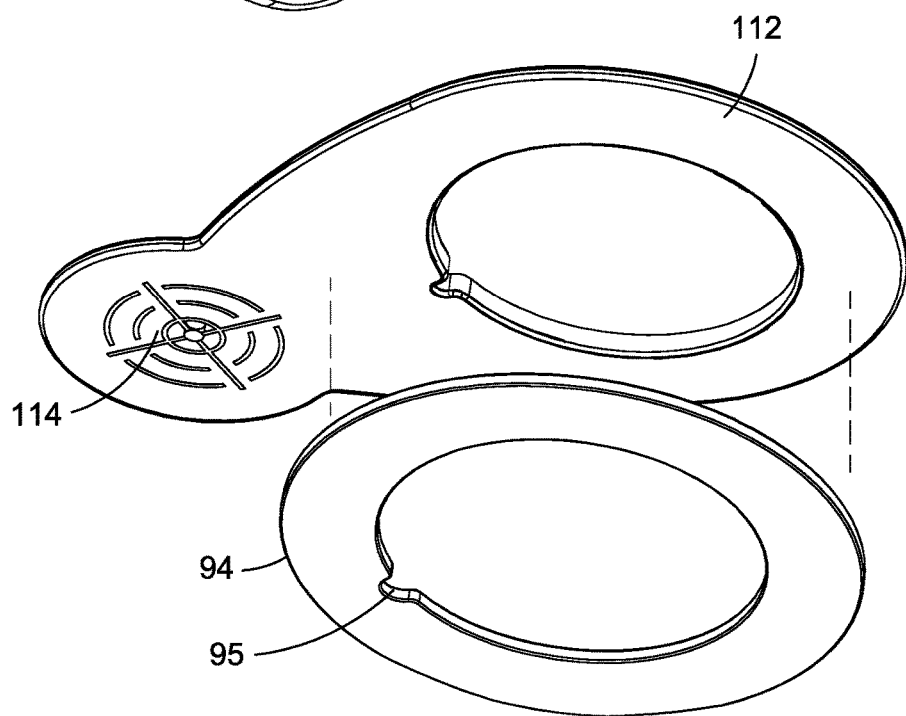
FIG. 34 is a collective view of a position guide, for positioning an annular metal member to a mobile device case.

Referring to FIGS. 33-34 there is shown a positioning guide 112. The guide 112 may be formed of a transparent plastic to aid in viewing structures behind the guide. Target indicia is printed or formed on the guide 112 to assist the user in positioning the ring 94 into a proper locate on the distal side 90 of the cell case 88. In operation, user places the target indicia over the cell phone case camera opening 92 to position the ring 94 into a proper location. A user then affixes the ring 94 using an adhesive backing. Once in proper place the use can connect the connector 86 to have proper alignment with a camera lens.

Referring to FIG. 35-40 there is shown a yet further embodiment of the disclosed subject matter wherein the interface is incorporated into a cell phone case to be used with an Android® type device. In particular a mobile phone 116 is capable of nesting into a mobile phone case 118 that includes an aperture that aligns with a camera lens (not shown) residing on the distal side of the mobile phone 116. A dermatoscope 122 is shown, with an eyepiece lens 124. In analog use of the dermatoscope 122 a medical practitioner looks through the lens 124 to observe an object 126, such as a patient's skin. In operation, using the connector device mobile phone case 118 to interface between the mobile device 116 and the dermatoscope 122, a user couples the connector device to the mobile phone case using the magnets (not shown and described in FIG. 36) formed in the mobile phone case 118 to mate with steel a ring 128 formed around the eyepiece lens 124 so that the lens (not shown) of the mobile device 116 is in alignment with the lens 126 through aperture 120. In this way, the lens (not shown) of the mobile device 116 captures an image through the dermatoscope lens 124 of an object 126. This allows the user to store images from the dermatoscope 122 into the memory of the mobile device 116, or otherwise, can view any object 126 on the mobile device 116 screen 117.

Figure 35:
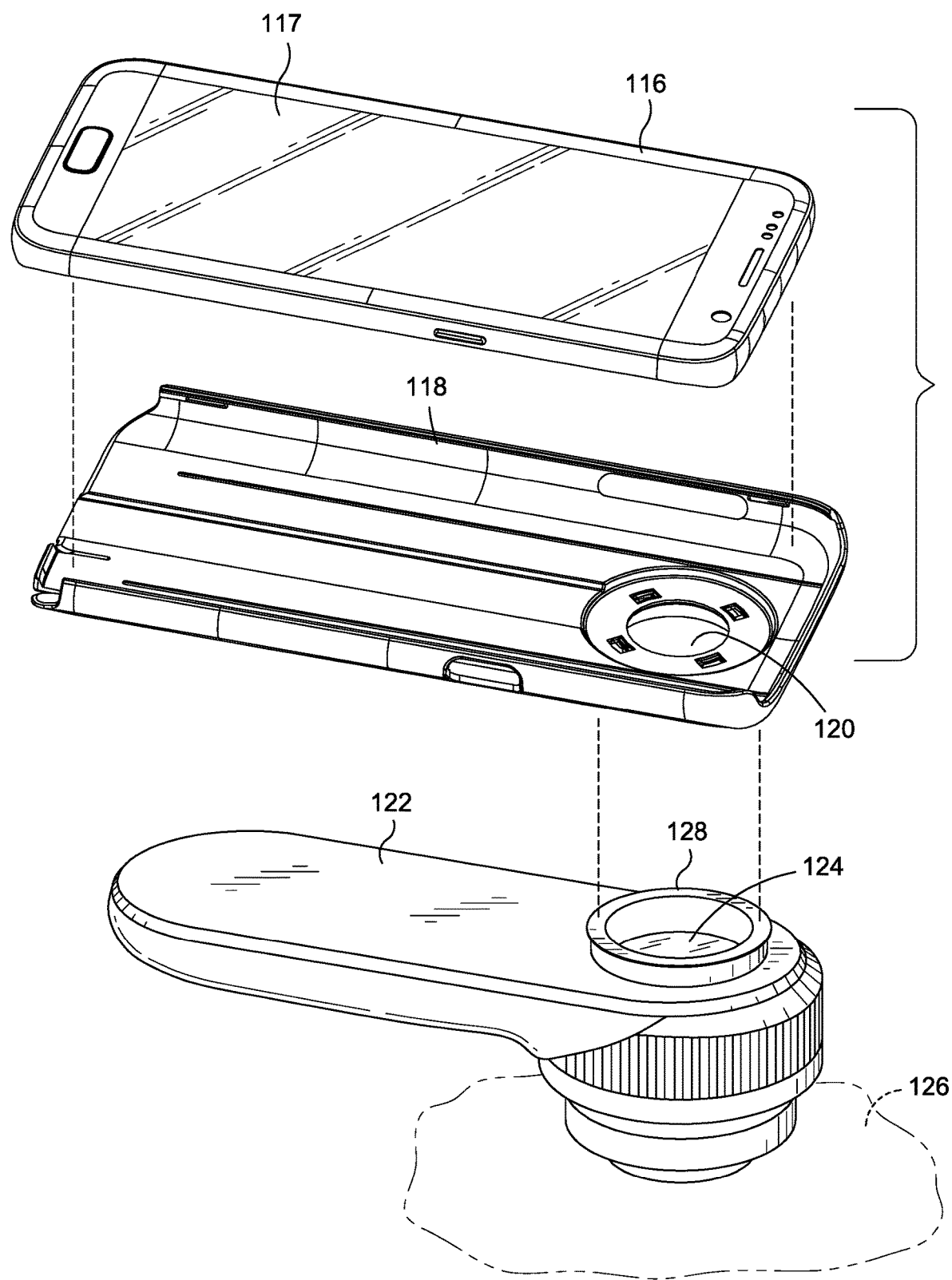
FIG. 35 is a further alternate embodiment of the attachment device incorporated into a cell phone case.
Figure 36:
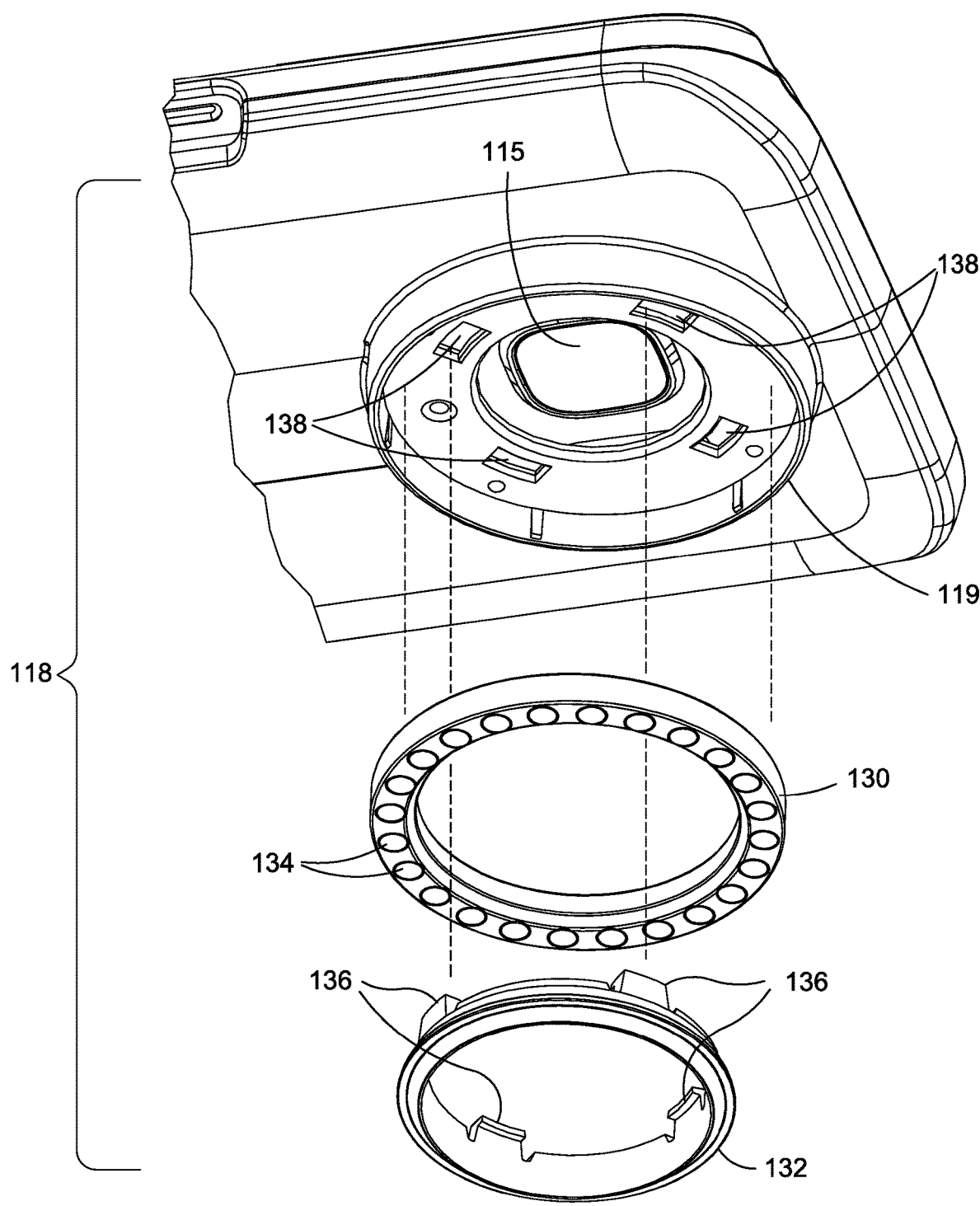
FIG. 36 is an exploded view of the further alternative embodiment of FIG. 35, showing an array of magnets and attachment mechanism.
Figure 40:
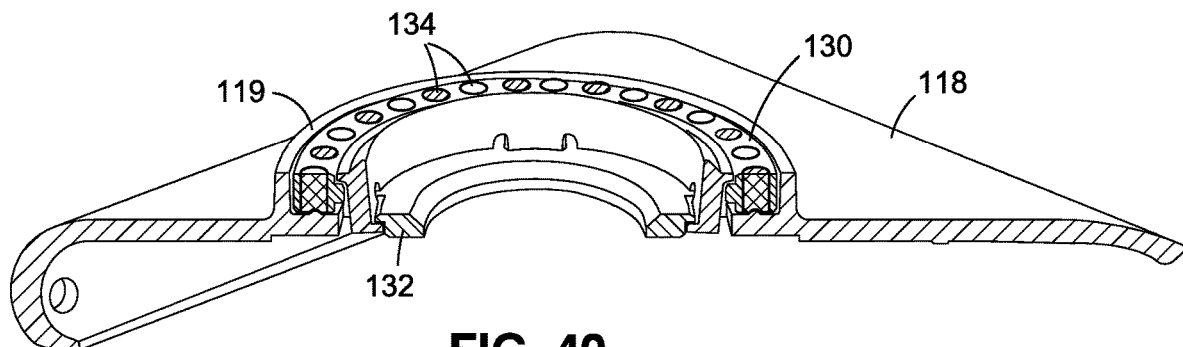
FIG. 40 is a cross-sectional view of the of the embodiment of FIGS. 35 and 36 when the magnetic array is attached to the mobile device cover.

Referring to FIG. 36 there is shown an exploded view of a portion mobile device case 118 from FIG. 35, viewed from the distal side of the case 118. A circular magnetic array 130 is inserted into a circular wall 119 formed on the distal side of case 118. The circular magnetic array 130 is secured by a circular insert 132, having four tabs 136 which are received into corresponding openings 138 formed in the case 118 to secure the magnetic array 130 into place into the case 118. The magnet array surrounds the mobile device 116 camera lens 115. FIG. 40 shows a cross section of the assembled elements 118, 130 and 132.

Figure 37:
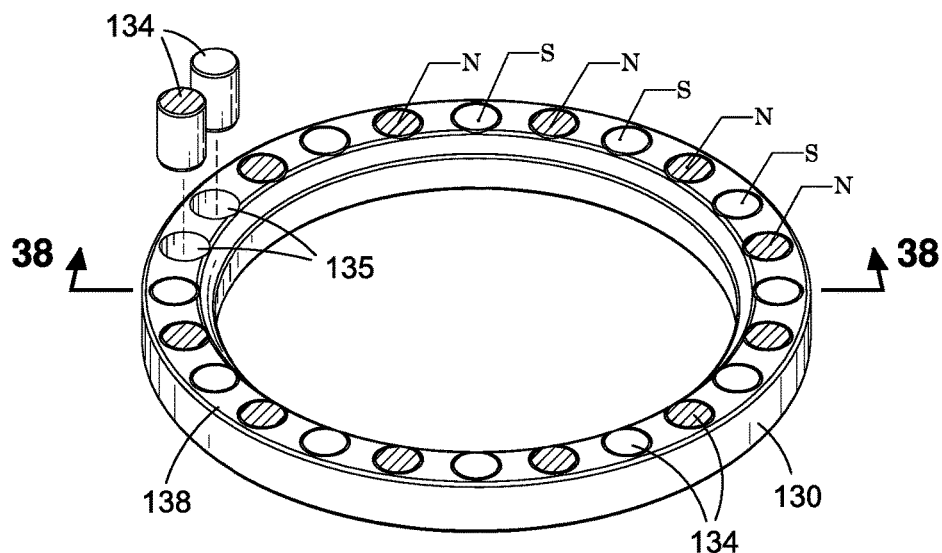
FIG. 37 is a view of the magnet array of the embodiment of FIGS. 35 and 36 showing magnets exploded from the array carrier and showing polarity.
Figure 38:
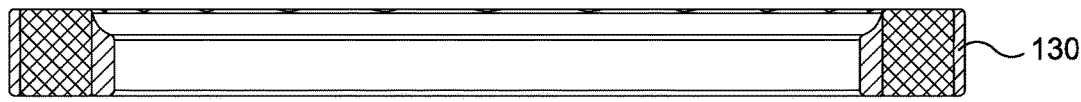
FIG. 38 is a cross sectional view of FIG. 37.
Figure 39:
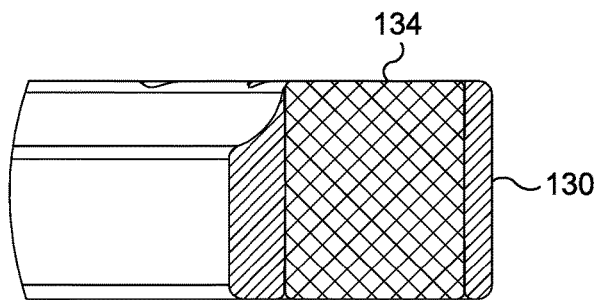
FIG. 39 is a close up cross-sectional view of FIGS. 37 and 38.

Referring to FIG. 37 there is shown the magnetic array 130 of FIG. 36, with two exemplary magnets 134 exploded from the annular carrier 138. The annular carrier is formed of substance, such as plastic, that does not significantly interact with the magnets 134. Magnets 134 may be rare earth magnets and may comprise neodymium, N42 grade ⅛ inch by ⅛-inch magnet with nickel plating. As shown, the magnets are cylindrical shaped. The magnets 134 are axially magnetized along the length of the cylinder shape with the poles having flat ends. Each of the magnets have corresponding recesses 135 formed in the annular carrier 138. Magnets 134 are pressed into place into recesses 135 for an interference fit, such the magnets 134 are fixed in place into the recesses 135. As described with regard to FIG. 35, the magnets 134 are designed to couple to one or more metal elements 128 fixed or formed around the eyepiece lens of a dermatoscope device 122 to hold the mobile device 116 in the case 118, onto a dermatoscope device 122 to align the mobile device camera lens 115 with eyepiece lens 124 of a dermatoscope device 122. As shown in FIG. 37 the magnets 134 are positioned in the annular carrier 138 in alternating polarity which can also be described as each magnet being positioned in antiparallel relation to adjacent magnets. In FIG. 37 the hatched magnets 134 represent magnets with the north polarity facing the distal side of the connector device 20, while magnets 134 not being hatched in the drawing represent magnets with the south polarity facing the distal side of the connector device 20. As described herein, the alternating polarity magnets reduce EMI by reducing magnetic flux around the connector device case 118, while increasing the magnetic flux strength close to the magnet poles. The antiparallel magnet arrangement maintains the near field forces while reducing the far field forces that may interfere with EMI sensitive equipment or devices, such as equipment and devices found in medical settings. FIG. 37 shows a cross section of FIG. 37, and FIG. 39 shows a closer view one end of the cross section of FIG. 38.

Figure 41:
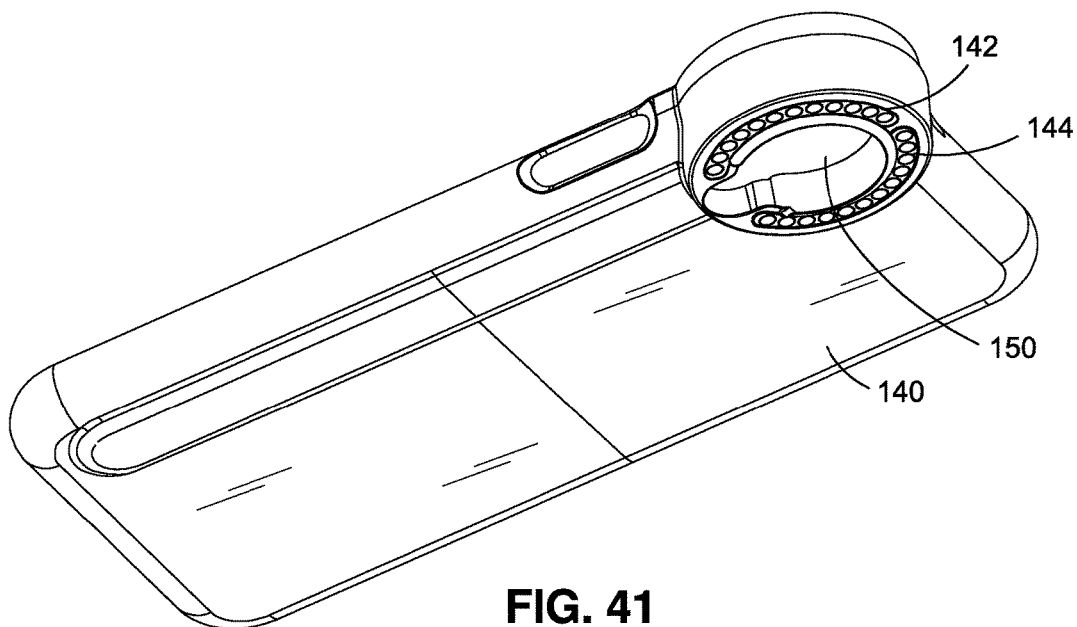
FIG. 41 is a further two piece alternate embodiment of the attachment device incorporated into a cell phone case where the magnetic array comprises two circular array elements.
Figure 42:
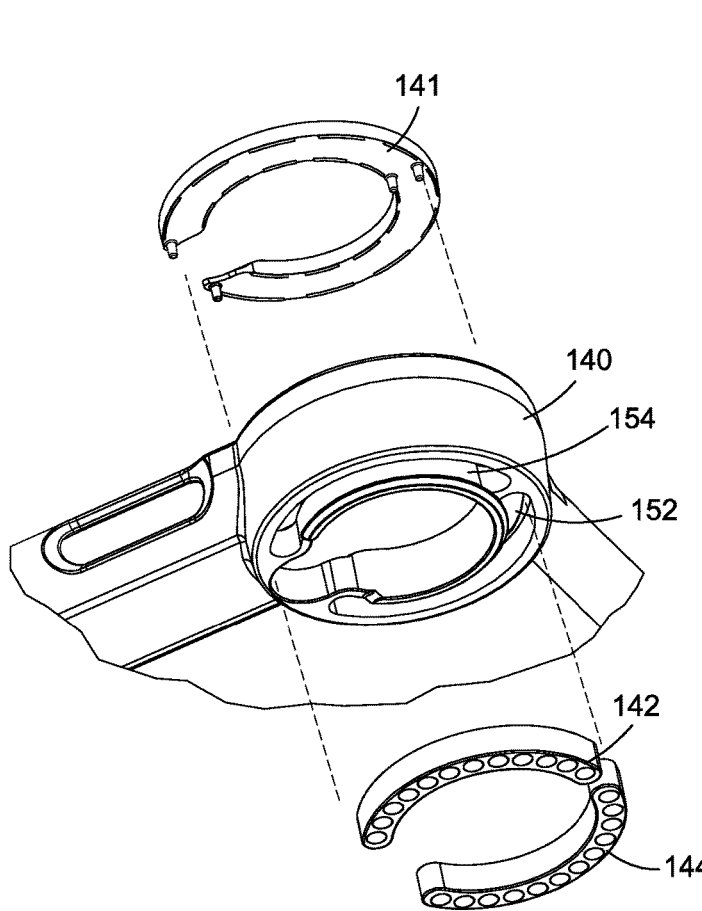
FIG. 42 is an exploded view of the embodiment of the attachment device of FIG. 41.
Figure 43:
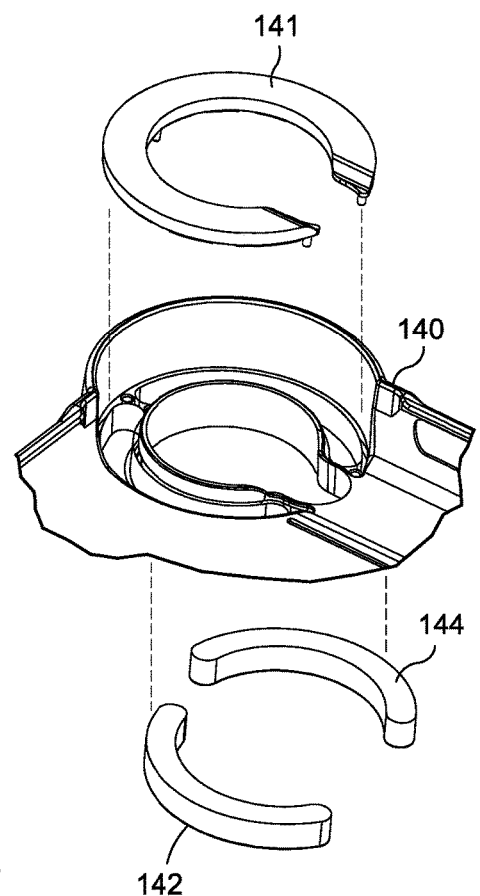
FIG. 43 is an exploded view of the embodiment the attachment device of FIG. 41, shown from an opposite view of FIG. 42.

Referring to FIG. 41 there is shown a dual array device of the disclosed subject matter that comprises a mobile device case 140 adapted for a mobile device where the camera is located in the upper corner of the device. FIG. 41 views the case 140 from the distal side, the side that will couple to a dermatoscope similar to described with regard to FIGS. 3 and 35 herein. A mobile device (not shown) may be nested into the case 140. Dual semi-circular magnetic arrays 142 and 144 are incorporated into the case 140. When a mobile device is inserted into the case 140, the magnetic arrays 142 and 144 surround the mobile device camera lens (not shown) through opening 150. Referring to FIG. 42 and there are shown an exploded views of a portion mobile device case 140 from FIG. 41, with FIG. 42 viewed from the distal side of the case 140 and FIG. 43 from the proximal side of the case 140. Two semi-circular magnetic arrays 142 and 144 are inserted into the case 140 into openings 152 and 154. A semicircular backing 141 is placed on the proximal side of the case 140 to hold the arrays 142 and 144 into place.

Figure 44:
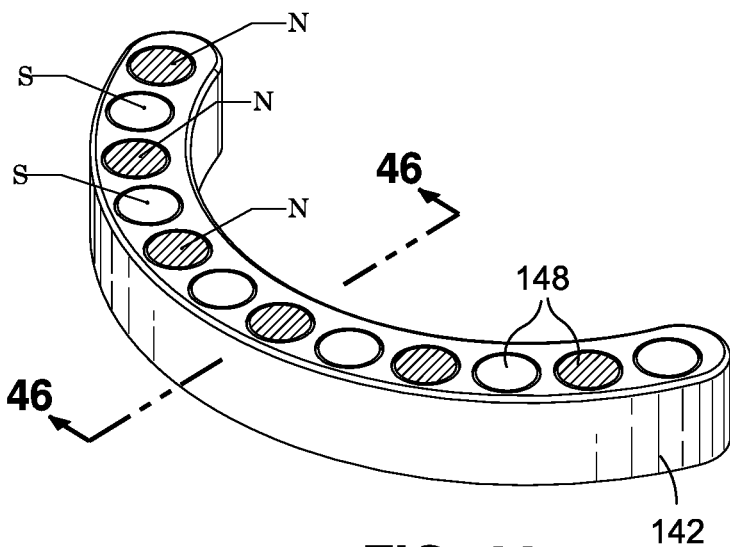
FIG. 44 is a view of one of the semicircular magnetic arrays of the embodiment of FIG. 41 showing the polarity of the magnets.
Figure 45:
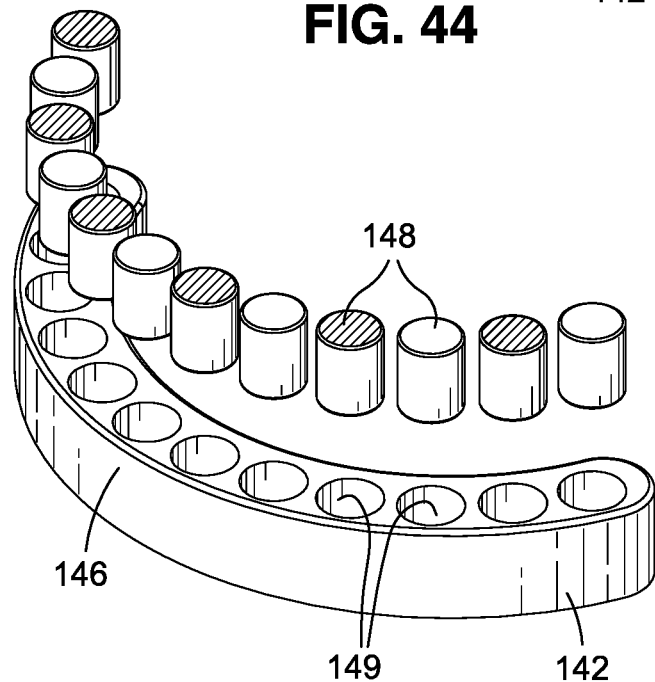
FIG. 45 is an exploded view of the semicircular magnetic array of FIG. 44, showing the magnets exploded from the array base.
Figure 46:
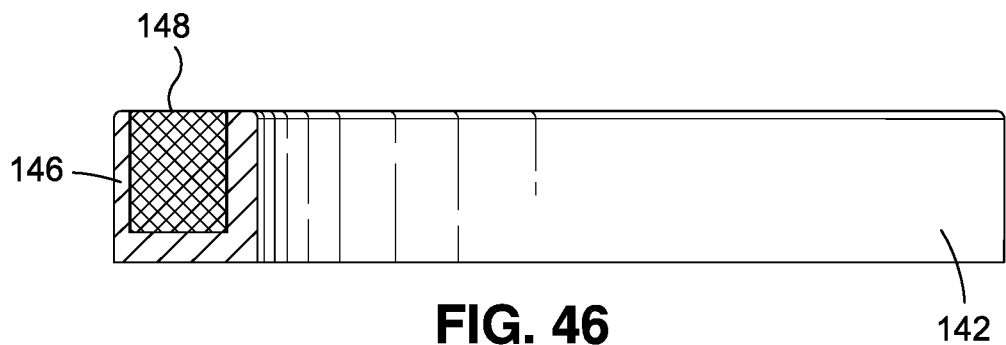
FIG. 46 is a cross-sectional view of FIG. 44.

Referring to FIGS. 44 and 45 there is shown an exemplary semi-circular magnetic array 142 (with magnetic array 144 being identical to 142 or alternatively a mirror image of the same). Magnets 148 are shown in the array 142, with FIG. 45 showing magnets 148 exploded from a semi-circular carrier 146. The carrier 146 is formed of substance, such as plastic, that does not significantly interact with the magnets 148. Magnets 148 may be rare earth magnets and may comprise neodymium, N42 grade ⅛ inch by ⅛-inch magnet with nickel plating. As shown, the magnets are cylindrical shaped. The magnets 148 are axially magnetized along the length of the cylinder shape with the poles having flat ends. Each of the magnets have corresponding recesses 149 formed in the carrier 146. Magnets 148 are pressed into place into recesses 149 for an interference fit, such the magnets 148 are fixed in place into the recesses 149. As described with regard to FIGS. 3 and 35, the magnets 148 are designed to couple to one or more metal elements fixed or formed around the eyepiece lens of a dermatoscope device to hold a mobile device in the case 140, onto a dermatoscope device to align the mobile device camera lens (not shown) with eyepiece lens a dermatoscope device (not shown). As shown in FIGS. 44 and 45 the magnets 148 are positioned in the carrier 146 in alternating polarity. In FIGS. 44 and 45 the hatched magnets 148 represent magnets with the north polarity facing the distal side of the arrays 142 and 144, while magnets 148 not being hatched in the drawing represent magnets with the south polarity facing the distal side of the arrays 142 and 144. As described herein, the alternating polarity magnets which can also be described as each magnet being positioned in antiparallel relation to adjacent magnets, reduce EMI by reducing magnetic flux around the connector device case 140, while increasing the magnetic flux strength close to the magnet poles. The antiparallel magnet arrangement maintains the near field forces while reducing the far field forces that may interfere with EMI sensitive equipment or devices, such as equipment and devices found in medical settings. FIG. 46 shows a cross section of FIG. 44.

Figure 47:
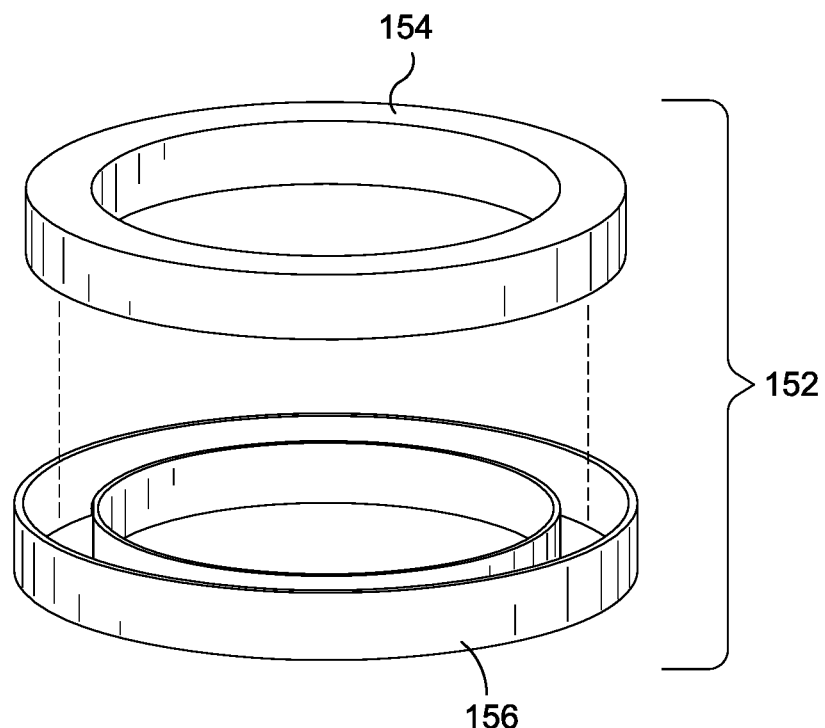
FIG. 47 is a view of an annular magnet incorporated into a ferromagnetic metal base.
Figure 48:
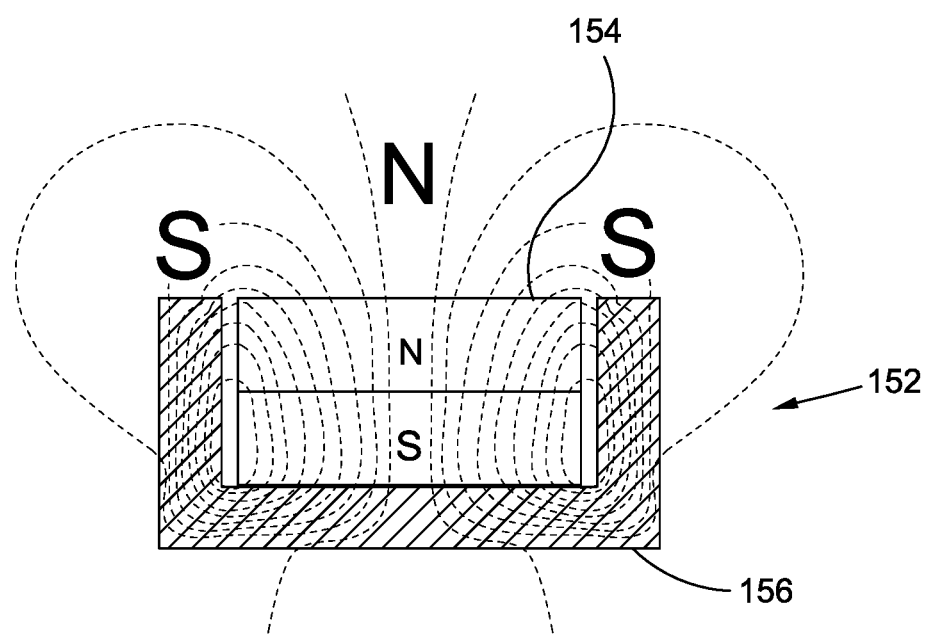
FIG. 48 is a view of the annular magnet with base of FIG. 48 showing a cross-sectional view and a graphical representation of magnetic flux.

Each of the described embodiments deploy cylindrically shaped magnets axially magnetized along the length of the cylinder, where the magnets are inserted into a carrier to form circular magnetic arrays or two semicircular magnetic arrays. The circular or near circular arrays are used as couplers to the eyepiece of a dermatoscope. The further alternative embodiment shown in FIGS. 47 and 48 provides a circular magnetic arrangement 152 that is formed using an annular magnet 154 that is axially magnetized. The magnet 154 is inserted into a circular three-sided case 156 that is formed of 0.5 mm thick 1018 mild steel. The assembly 152 creates a pot magnet effect, greatly reducing the stray magnetic flux. As such, the assembly 152 may be used in place of any of the circular or near circular magnetic arrays herein to provide a connector with reduced EMI by reducing magnetic flux around the assembly 152 and with increased magnetic flux at the point of contact. In this embodiment the exposed north side of the magnet would be used to interface with a metal element in the eyepiece of the dermatoscope. The magnet and casing arrangement of FIGS. 47 and 48 maintains the near field forces while reducing the far field forces that may interfere with EMI sensitive equipment or devices, such as equipment and devices found in medical settings. It is contemplated that the N/S arrangement as shown in FIG. 48 would have equal effect and results if the polarity of the magnet 154 was reversed.

Referring collectively to FIGS. 49-57, disclosed is a further embodiment of an attachment apparatus 158 to couple a mobile device 160 to a lens of a medical device (not shown) to capture and view images. In operation a ferromagnetic steel ring 162 is adhered to the mobile device 160 surface. The ring 162 is placed at an appropriate distance from the desired camera lens 164 so that the aperture 166 of the attachment apparatus 158 can encircle the camera lens 164. The mobile device 160 shown may be an iPhone® 11, manufactured by Apple Corp. that places the lens 164 in the location shown in FIG. 49. In this regard, in use, the ring 162 center is placed 40 mm away from the center of the lens 164. However, in early models of the iPhone®, the appropriate placement of the ring 162 center may be 30 mm away from the lens center due to the camera lens being situated at a different location. Although the representative distances as disclosed herein are 40 mm and 30 mm, it is understood and contemplated herein that distance may vary from the stated distances depending on the location of a camera lens on the mobile device and variations in the length of the attachment apparatus 158. As such, the attachment apparatus 158 provides a mechanism to place the center of the aperture 166 at two different distances from the center of the carrier aperture 182 the desired distance depending on the mobile device model.

Figure 49:
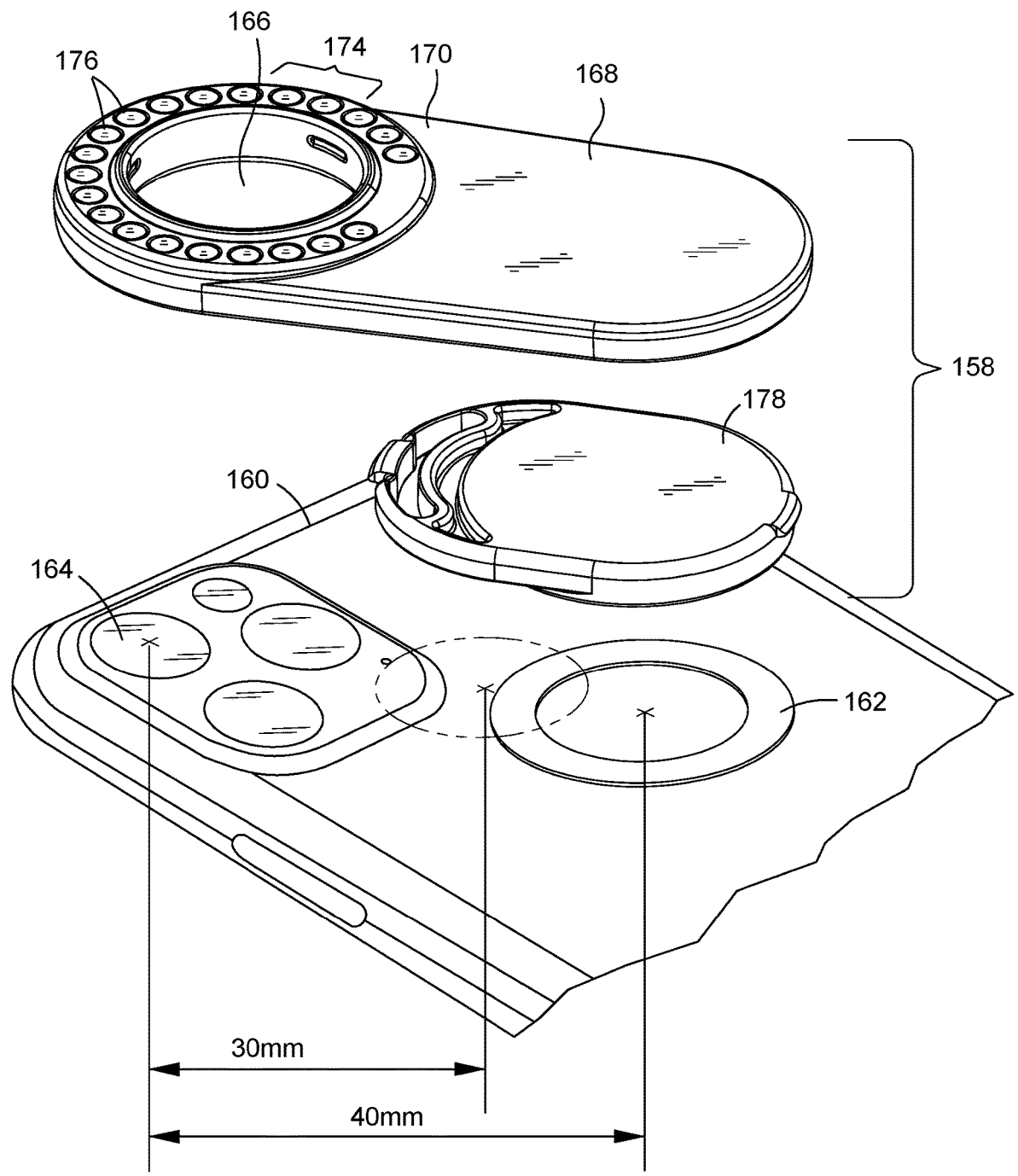
FIG. 49 is a view of the component parts of a further embodiment of the attachment device showing distances of a camera lens of mobile device.
Figure 50:
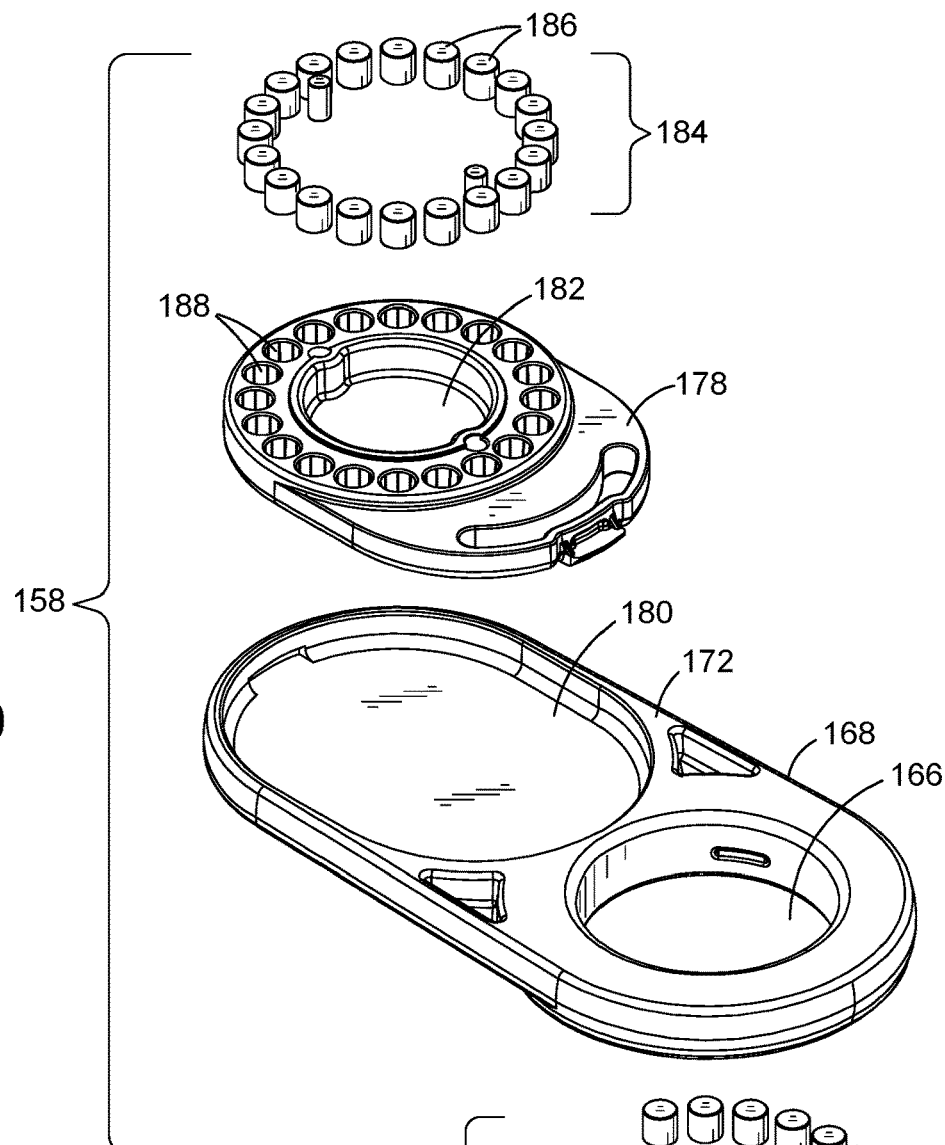
FIG. 50 is an exploded view of the attachment device of FIG. 49.
Figure 51:
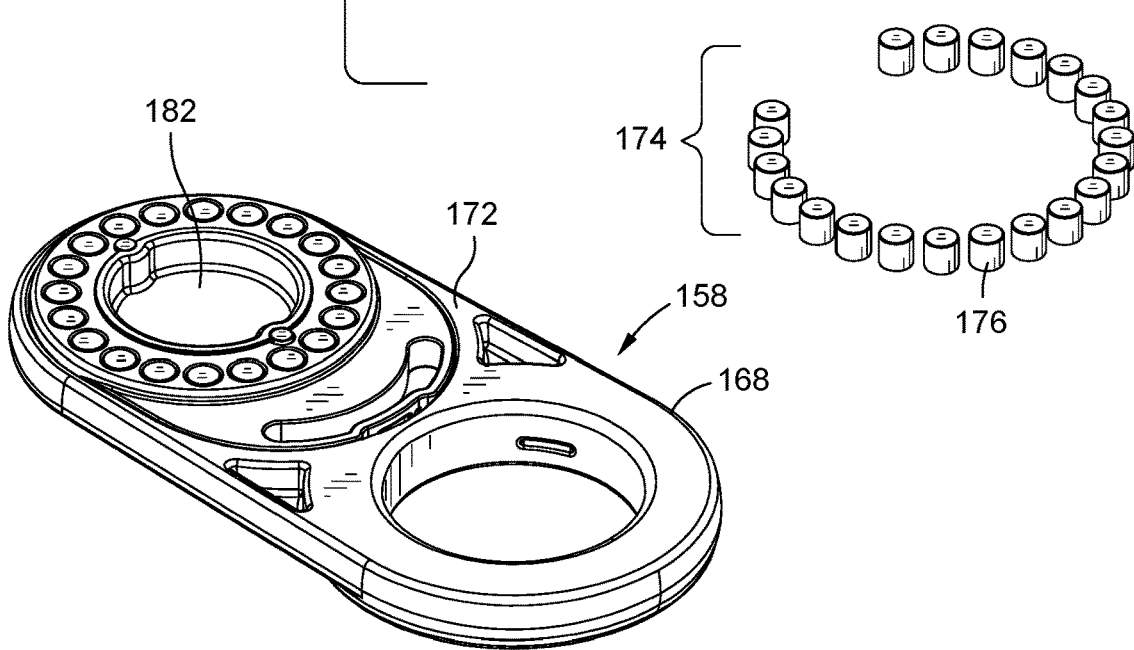
FIG. 51 is view of the proximal side of the attachment device of FIG. 49.
Figure 52:
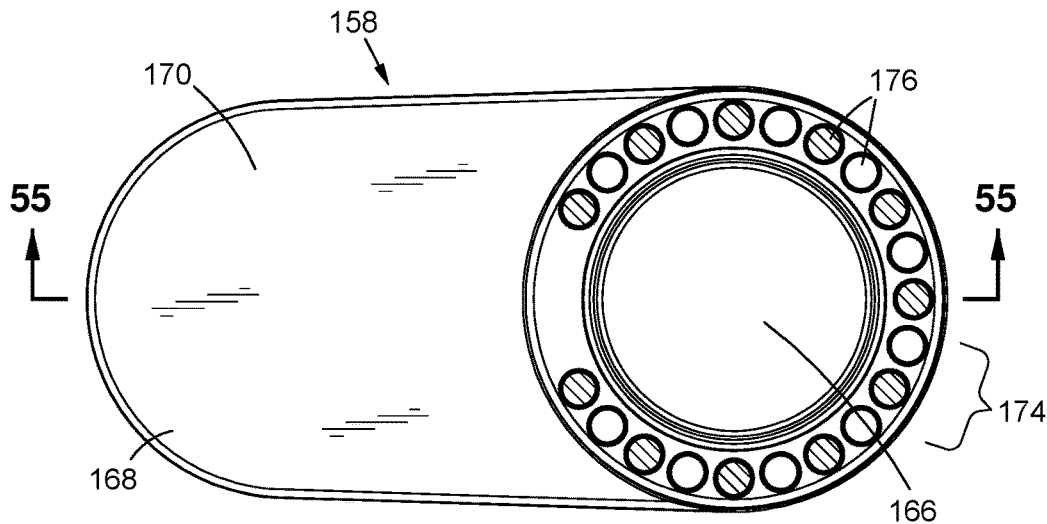
FIG. 52 is a view of the of the distal side of the attachment device of FIG. 49.

The attachment apparatus 158 includes an attachment body 168 having a distal side 170 for attaching to a medical device (not shown) and a proximal side 172 for attaching to the mobile device 160. The distal side as best shown in FIGS. 49, 50 and 52, is adapted to engage a steel ring (not shown) that may surround a lens of a medical device (not shown). Referring particularly to FIGS. 49, 50 and 52 there is shown a magnetic array 174 of an annular arrangement of axially magnetized magnets 176 positioned in the attachment body 168. The attachment body 168 may be formed from a non-ferromagnetic or non-metallic substance, such as plastic, that does not significantly interact with the magnetic field. Each of the axially magnetized magnets 176 are positioned in antiparallel relation to an adjacent magnet. As shown in FIG. 52, the hatched magnets 176 show north pole of the magnet facing upward and the magnets 176 without the hatching show the south pole of the magnet facing upward. As described herein the antiparallel arrangements of the magnets 176 reduce magnetic flux and strengthen the magnetic attraction at the point of contact with a steel ring formed on the medical device (not shown). In addition, the cylindrical shape magnets 176 are received into apertures (not shown) in the attachment body 168, via crush ribs or other mechanism to hold the magnets 176 securely in place.

Figure 53:
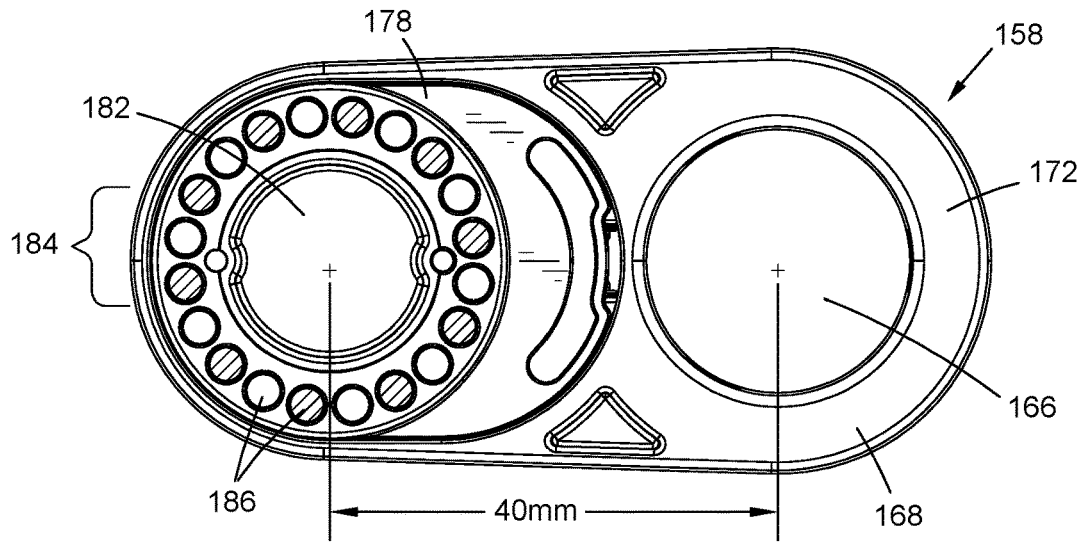
FIG. 53 is a view of the proximal side of the attachment device of FIG. 49 showing the magnetic array centered at 40 mm.
Figure 54:
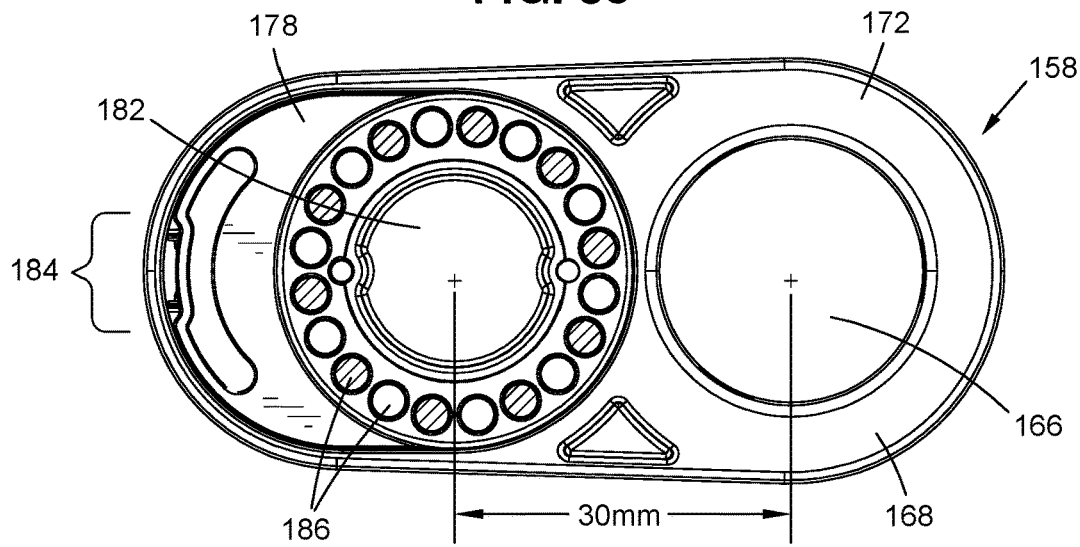
FIG. 54 is a view of the proximal side of the attachment device of FIG. 49 showing the magnetic array centered at 30 mm.
Figure 55:
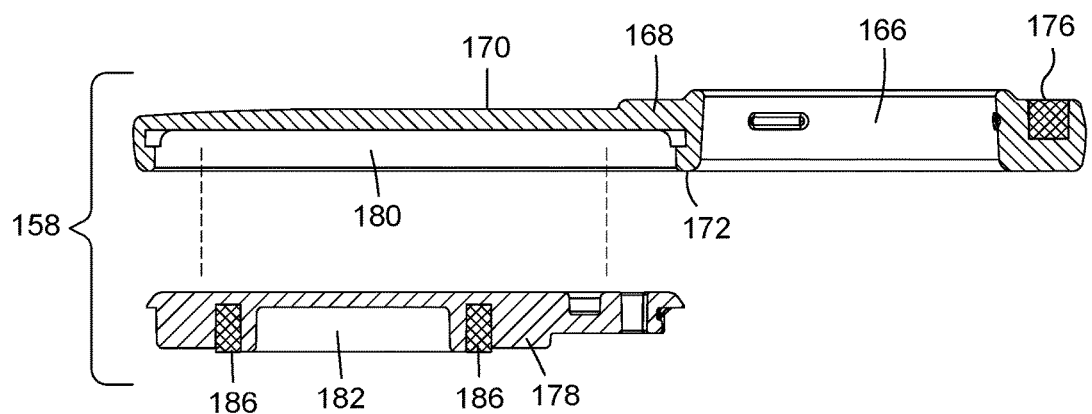
FIG. 55 is a cross sectional view of the attachment device of FIG. 49 showing the proximal side magnetic array exploded from the main body.
Figure 56:
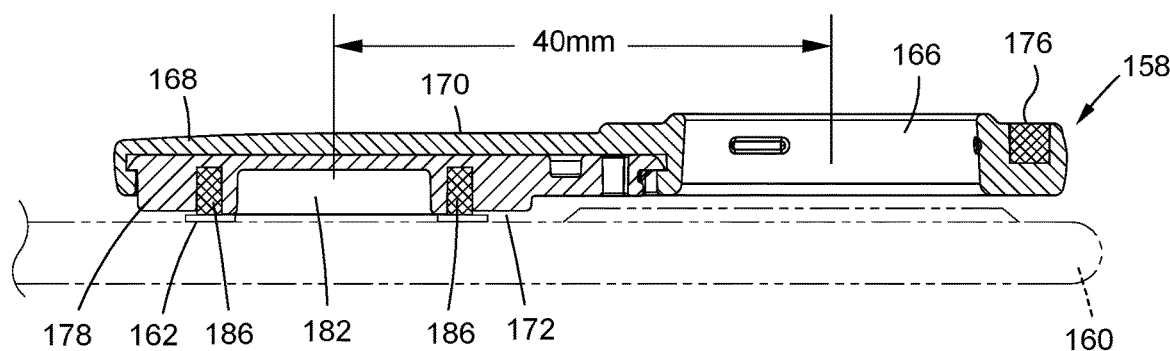
FIG. 56 is a cross sectional view of the attachment device of FIG. 49 showing the proximal side magnetic array centered at 40 mm.
Figure 57:
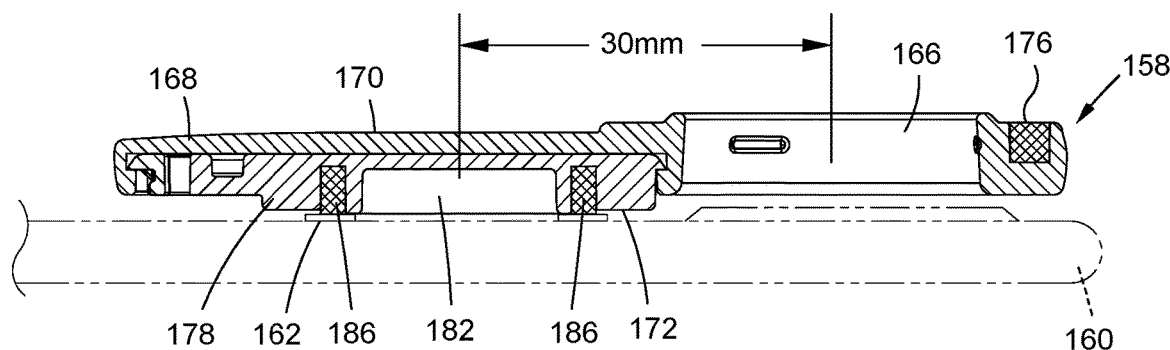
FIG. 57 is a cross sectional view of the attachment device of FIG. 49 showing the proximal side magnetic array centered at 30 mm.

The attachment apparatus 158 includes a magnetic array carrier 178 that is received into a receiving aperture 180 formed in the attachment body 168, to nest within the attachment body 168 on the proximal side 172 of the attachment body 168. The aperture 180 and the array carrier 178 are both adapted to receive the carrier 178 in two separate directions. The first direction as shown in FIGS. 53 and 56 creates a 40 mm distance between the center of the aperture 166 and carrier aperture 182. The second direction as shown in FIGS. 54 and 57 show creates a 30 mm distance between the center of the aperture 166 and the carrier aperture 182 to be usable with the latest iPhone® model and earlier iPhone® models. Distances may vary according to the mobile device to which the attachment apparatus 158 is adapted, or the length of the attachment apparatus 158. FIG. 55 shows the array carrier 178 exploded away from the attachment body 168, as the carrier 178 is detachable and may be snap fit into aperture 180 in either direction. The carrier 178 includes a raised surface where the magnets 186 are attached, so that when the carrier 178 is attached to the ring 162, and nested into the aperture 180 of the attachment body 168, the attachment body 168 is positioned with enough clearance above the surface of the mobile device 160 so as to not interfere with raised surfaces that may be formed on the surface of the mobile device that may surround or be integral with the mobile device 160 camera lens as shown in FIGS. 56 and 57.

Referring particularly to FIGS. 50, 53 and 54 the magnetic array 184 may be formed from axially magnetized magnets 186, wherein each of the axially magnetized magnets 186 are positioned in antiparallel relation to an adjacent magnet. The magnetic array carrier 178 may be formed from a non-ferromagnetic or non-metallic substance, such as plastic, that does not significantly interact with the magnetic field. As shown in FIGS. 53 and 54, the hatched magnets 186 show north pole of the magnet facing upward and the magnets 186 without the hatching show the south pole of the magnet facing upward. As described herein the antiparallel arrangements of the magnets 186 reduce magnetic flux and strengthen the magnetic attraction at the point of contact with the steel ring 162. In addition, the cylindrical shape magnets 186 are received into apertures 188 formed in the carrier 178, via crush ribs or other mechanism to hold the magnets 186 securely in place.

Figure 58:
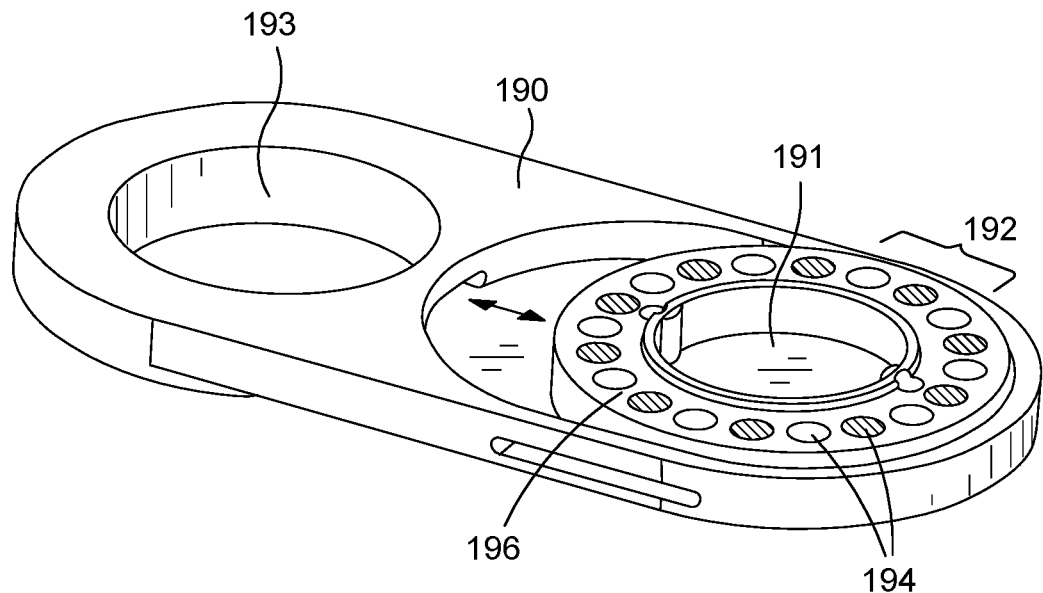
FIG. 58 is a view of a further embodiment of the attachment device wherein the proximal side magnetic array is slidably movable, and is shown centered in a 40 mm position.
Figure 59:
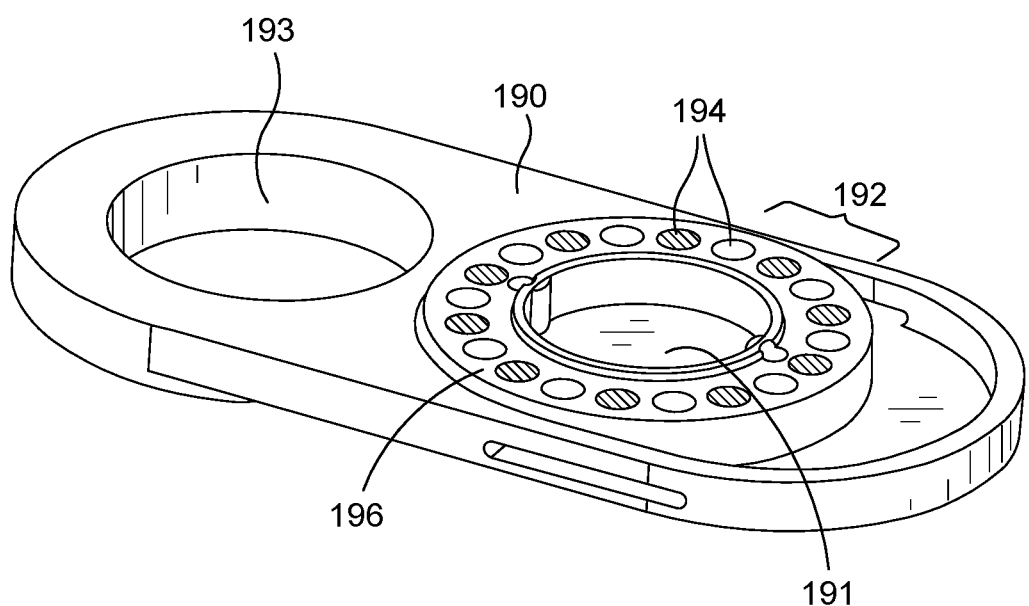
FIG. 59 is a view of the attachment device of FIG. 58 wherein the proximal side magnetic array is shown centered in a 30 mm position.

Referring particularly to FIGS. 58 and 59 there is shown a further embodiment of an attachment device 190 that operates similar to the embodiment described with respect to FIGS. 49-57, to place the attachment device 190 in a proper location depending on the mobile device camera placement, except that the proximal side magnetic array 192 is slidably movable to a first extended position, 40 mm between center aperture 191 and device aperture 193 as shown in FIG. 58 and a second reduced position, 30 mm between center aperture 191 and device aperture 193 as shown in FIG. 59. Distances may vary from the distances stated herein according to the mobile device to which the attachment device 190 is adapted, or the length of the attachment apparatus 190. The magnetic array 192 may be formed from axially magnetized magnets 194, wherein each of the axially magnetized magnets 194 are positioned in antiparallel relation to an adjacent magnet. The magnetic array carrier 196 may be formed from a non-ferromagnetic or non-metallic substance, such as plastic, that does not significantly interact with the magnetic field. As shown in FIGS. 58 and 59, the hatched magnets 194 show north pole of the magnet facing upward and the magnets 194 without the hatching show the south pole of the magnet facing upward. As described herein the antiparallel arrangements of the magnets 194 reduce magnetic flux and strengthen the magnetic attraction at the point of contact with the steel ring (not shown). In addition, the magnets 194 are received into apertures (not shown) formed in the carrier 196, via crush ribs or other mechanism to hold the magnets 194 securely in place.

Figure 60:
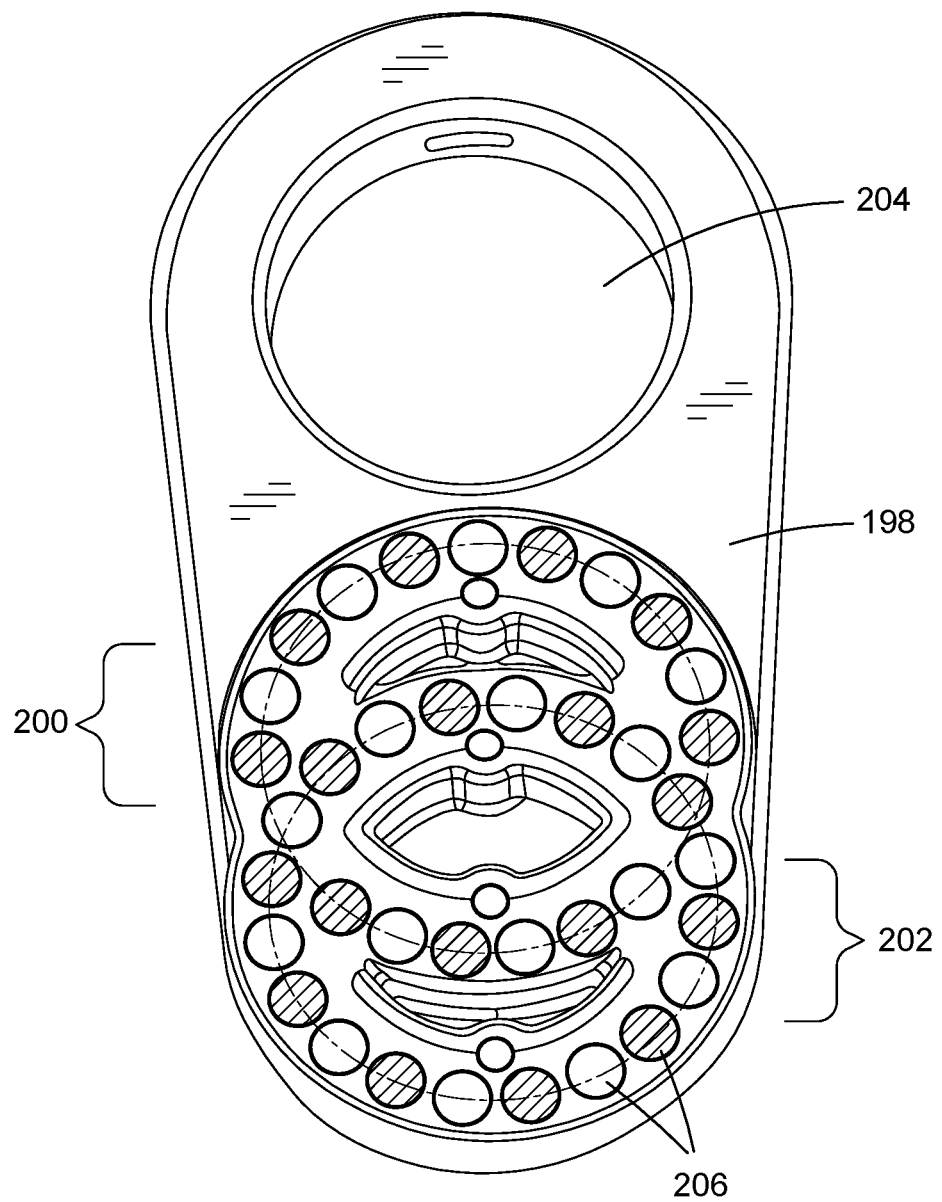
FIG. 60 is a view of a further embodiment of the attachment device wherein the proximal side magnetic array has two intersected circular magnetic arrays for positioning the attachment body at first and second distances.

Referring particularly to FIG. 60 there is shown a further embodiment of an attachment device 198 that incorporates two overlapping magnetic array rings 200 and 202 formed in the proximal side of the device 198 to attach to a mobile device (not shown). The two rings 200 and 202 operates similar to the embodiment described with respect to FIGS. 49-57, to place the attachment device 198 in a proper location depending on the mobile device camera placement, except that the proximal side magnetic array comprises two overlapping magnetic array rings 200 and 202, wherein if the magnetic array ring 200 engages a steel ring (not shown) attached to a mobile device, the center of aperture 204 is placed 30 mm to the center of ring 200. Likewise, if the magnetic ring array ring 202 engages a steel ring (not shown) attached to a mobile device the center of the aperture 204 is placed 40 mm to the center of ring 202. Distances may vary from the distances stated herein according to the mobile device to which the attachment device 198 is adapted, or the length of the attachment apparatus 198. The magnetic arrays 200 and 202 may be formed from axially magnetized magnets 206, wherein each of the axially magnetized magnets 206 are positioned in antiparallel relation to an adjacent magnet. The magnetic attachment device 198 may be formed from a non-ferromagnetic or non-metallic substance, such as plastic, that does not significantly interact with the magnetic field. As shown in FIG. 60, the hatched magnets 206 show north pole of the magnet facing upward and the magnets 206 without the hatching show the south pole of the magnet facing upward. As described herein the antiparallel arrangements of the magnets 206 reduce magnetic flux and strengthen the magnetic attraction at the point of contact with the steel ring (not shown). In addition, the magnets 206 are received into apertures (not shown) formed in the device 198, via crush ribs or other mechanism to hold the magnets 206 securely in place.

The above description is given by way of example, and not limitation. Given the above disclosure, one skilled in the art could devise variations that are within the scope and spirit of the disclosure herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:
1. An attachment apparatus for optically coupling a mobile device camera to a lens of a medical examination device, said apparatus comprising:
an attachment body, said attachment body comprising:
a proximal side for attaching to a mobile device, said proximal side comprising a first array of magnets, said first array of magnets being releasably detach- able from the attachment body and reversibly positionable on the body to a first position and a second position; and a distal side for attaching to a medical examination device, said distal side comprising a second array of magnets positioned radially around an aperture.

2. The apparatus of claim 1 wherein said first array of magnets comprises at least one pair of axially magnetized magnets, said at least one pair of axially magnetized magnets positioned in antiparallel arrangement relative to each other.

3. The apparatus of claim 1 wherein the second array of magnets comprises at least one pair of axially magnetized magnets, said at least one pair of axially magnetized magnets positioned in antiparallel arrangement relative to each other.

4. The apparatus of claim 1 wherein said first array of magnets comprises a plurality of pairs of axially magnetized magnets, each of said pairs of axially magnetized magnets are positioned in antiparallel arrangement relative to the other paired magnet.

5. The apparatus of claim 1 wherein said second array of magnets comprises a plurality of pairs of axially magnetized magnets, each of said pairs of axially magnetized magnets are positioned in antiparallel arrangement relative to the other paired magnet.

6. The apparatus of claim 1 wherein said first array of magnets further comprises a plurality of axially magnetized magnets positioned radially around an aperture wherein each axially polarized magnet is positioned in antiparallel arrangement relative to each adjacent axially magnetized magnet.

7. The apparatus of claim 1 wherein said second array of magnets wherein each axially polarized magnet is positioned in antiparallel arrangement relative to each adjacent axially magnetized magnet.

8. The apparatus of claim 1 wherein said medical examination device incorporates at least one ferromagnetic metal element capable of magnetically coupling with said second array of magnets.

9. The apparatus of claim 1 wherein said mobile device incorporates at least one ferromagnetic metal element capable of magnetically coupling with said first array of magnets.

10. The apparatus of claim 8 wherein said at least one ferromagnetic metal element is formed surrounding a lens of a medical examination device.

11. The apparatus of claim 1 wherein said magnets are cylindrical shaped.

12. The apparatus of claim 1 where said magnets are neodymium magnets.

13. The apparatus of claim 1 wherein said magnets have nickel plating.

14. An attachment apparatus for optically coupling a mobile device camera to a lens of a medical optical device, said apparatus comprising:

an attachment body;

a first magnetic array formed about an aperture and releasably detachable from said attachment body said first magnetic array magnets comprising at least one pair of axially magnetized magnets positioned in antiparallel arrangement relative to each other; and wherein said first magnetic array is attachable to the attachment body in a first position or in a second position to align the aperture with the mobile device camera lens.

15. The apparatus of claim 14 wherein said attachment body has a proximal side and a distal side, the proximal side for attaching to the mobile device and a distal side for attaching to the medical device and further comprising a second of array of magnets positioned on the proximal side of the attachment body, said second array of magnets formed on the proximal side of the attachment body comprising at least one pair of polarized magnets, said at least one pair of magnets positioned in antiparallel arrangement relative to each other.

16. The apparatus of claim 15 wherein said magnets of the second array of magnets are axially magnetized magnets.

17. The apparatus of claim 16 wherein said medical optical device incorporates at least one ferromagnetic metal element capable of magnetically coupling with said magnets.

18. The apparatus of claim 17 wherein said at least one ferromagnetic metal element is formed surrounding a lens of the medical optical device for magnetically coupling the aperture of first magnetic array in alignment with a lens of the optical device.

19. The apparatus of claim 14 wherein said magnets are cylindrical shaped.

20. The apparatus of claim 14 wherein said magnets are neodymium.

21. The apparatus of claim 14 wherein said magnets have nickel plating.

* * * * *